(12) United States Patent
de Béthune et al.

(10) Patent No.: US 6,528,251 B2
(45) Date of Patent: Mar. 4, 2003

(54) METHOD OF MANAGING THE CHEMOTHERAPY OF PATIENTS WHO ARE HIV POSITIVE BASED ON THE PHENOTYPIC DRUG SENSITIVITY OF HUMAN HIV STRAINS

(75) Inventors: Marie-Pierre de Béthune, Everberg (BE); Kurt Hertogs, Antwerp (BE); Rudi Pauwels, Weerde (BE)

(73) Assignee: Virco N.V., Mechelen (BE)

( * ) Notice: Subject to any disclaimer, the term of this patent is extended or adjusted under 35 U.S.C. 154(b) by 53 days.

(21) Appl. No.: 09/735,487

(22) Filed: Dec. 14, 2000

(65) Prior Publication Data

US 2002/0042679 A1 Apr. 11, 2002

Related U.S. Application Data

(62) Division of application No. 09/117,217, filed as application No. PCT/IB97/00071 on Jan. 24, 1997, now Pat. No. 6,221,578.

(30) Foreign Application Priority Data

Jan. 26, 1996 (EP) ............................................. 96200175

(51) Int. Cl.[7] .................................................. C12Q 1/70
(52) U.S. Cl. ..................... 435/5; 435/252.1; 435/320.1; 440/476; 514/44; 536/23.1
(58) Field of Search ........................ 514/44; 536/23.1; 435/320.1, 252.1, 5; 440/476

(56) References Cited

U.S. PATENT DOCUMENTS

| | | | |
|---|---|---|---|
| 3,875,396 | A | 4/1975 | Webb |
| 5,344,846 | A | 9/1994 | Jackus et al. |
| 5,401,629 | A | 3/1995 | Harpold et al. |
| 5,569,588 | A | 10/1996 | Ashby et al. |
| 5,665,577 | A | 9/1997 | Sodroski et al. |
| 5,733,720 | A | 3/1998 | Olivo |
| 5,837,464 | A | 11/1998 | Capon et al. |
| 5,851,757 | A | 12/1998 | Olivo et al. |
| 5,856,086 | A | 1/1999 | Kozal et al. |
| 5,939,253 | A | 8/1999 | Scholl et al. |
| 5,945,276 | A | 8/1999 | Wu et al. |

FOREIGN PATENT DOCUMENTS

| | | |
|---|---|---|
| WO | WO9014427 | 11/1990 |
| WO | WO9401584 | 1/1994 |
| WO | WO9608580 | 3/1996 |
| WO | WO9712220 | 4/1997 |
| WO | WO9727319 | 7/1997 |
| WO | WO9845704 | 10/1998 |
| WO | WO9846796 | 10/1998 |
| WO | WO9859074 | 12/1998 |
| WO | WO9930154 | 6/1999 |

OTHER PUBLICATIONS

Jeffrey Rubnitz et al., Molecular and Cellular Biology, vol. 4, No. 2 (1984) pp. 2253–2258.
Kellam et al., Antimicrobial Agents and Chemotherapy, vol. 38, No. 1 (1994) pp. 23–30.
Japour et al., Antimicrobial Agents and Chemotherapy, vol. 37, No. 5 (1993) pp. 1095–1101.
Maschera et al., J. of Virology, vol. 69, No. 9 (1995) pp. 5431–5436.
Roberts, AIDS, vol. 9, No. Suppl. 2 (1995) pp. S27–S32.

*Primary Examiner*—Kenneth R. Horlick
*Assistant Examiner*—Young Kim
(74) *Attorney, Agent, or Firm*—Birch, Stewart, Kolasch & Birch, LLP.

(57) ABSTRACT

The present invention is drawn to A method of managing HIV chemotherapy of patients who are HIV positive, which comprises transfecting a cell line susceptible to infection by HIV with a sequence from the pol gene of HIV, which sequence encodes a desired target enzyme, obtained by isolating viral RNA from a sample of a biological material from a patient and reverse transcribing the desired region of said pol gene, and a HIV-DNA construct from which said sequence has been deleted, culturing said transfected cells so as to create a stock of chimeric viruses providing an indication of the resistance profile of the circulating virus, assessing the phenotypic sensitivity of said chimeric viruses to an inhibitor of said enzyme encoded by the pol gene of HIV and assigning a value thereto, constructing a data set comprising said value for chimeric virus sensitivity and the corresponding value for a chimeric wild-type strain of HIV, repeating the sensitivity assessment for at least two further inhibitors and thereby constructing at least three such data sets in total, representing said data sets in two dimensional or three dimensional graphical form such that the difference between the chimeric and wild-type sensitivities in the case of each data set provides a visual measure of the resistance of the chimeric stock to treatment by the inhibitor in question, and selecting the optimum inhibitor(s) on the basis of the graphical representation of the resistance so measured.

12 Claims, 35 Drawing Sheets

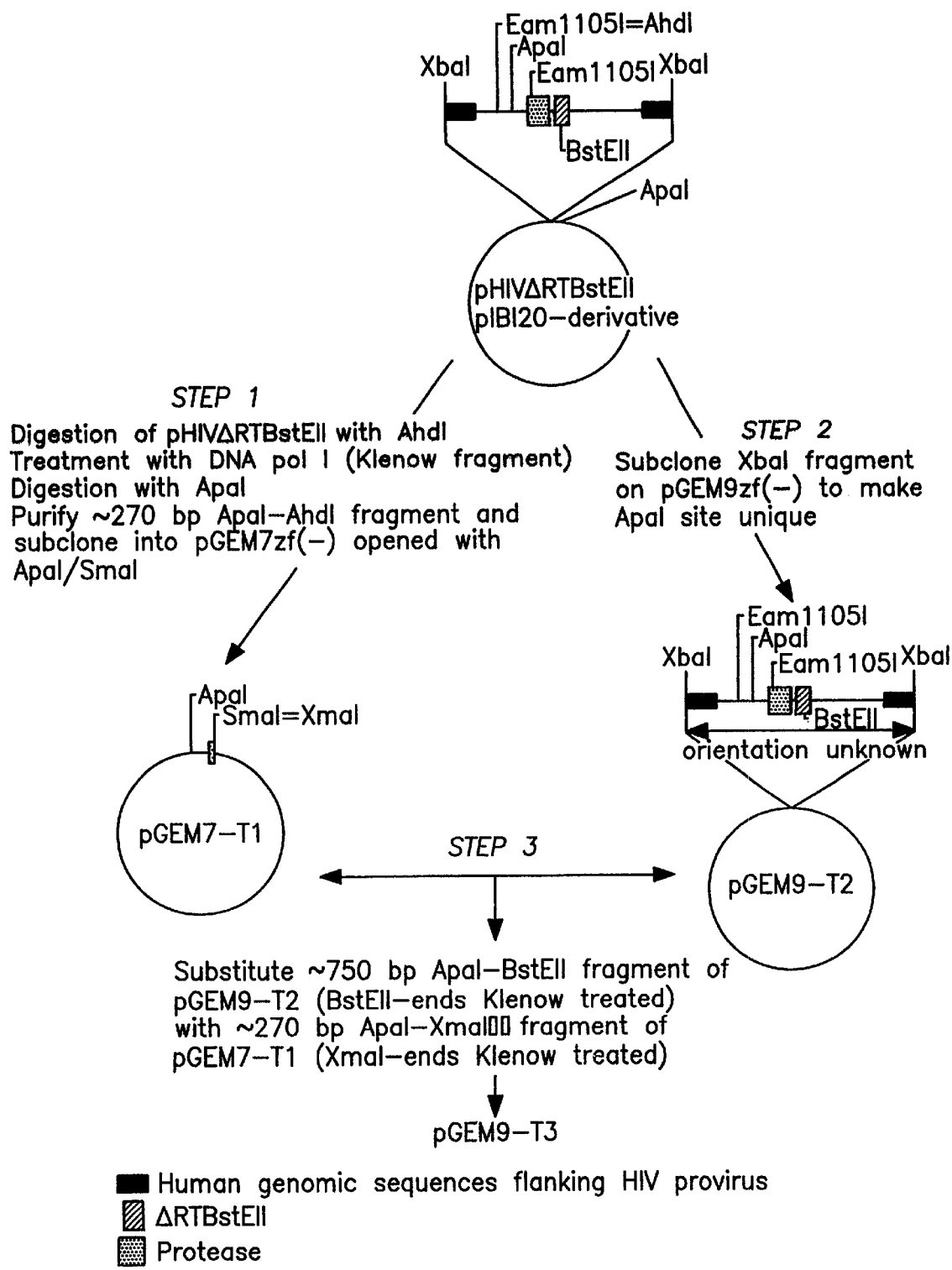

FIG. 2

STEP 1
5'-GACNNN/NNGTC (AhdI recognition sequence and cleavage site)
5'-GACCCC/TCGTC (AhdI site at the beginning of the protease coding region)

AhdI cleavage
Removal of 1-nucleotide 3'-overhang
by treatment with DNA polymerase I
(Klenow fragment)

5'-GACCC ←→ 5'-CCC/GGG (SmaI)

ligation of blunt ends
restores the SmaI site

STEP 3
5'-GAC/CCGGG

5'-G/GTNACC (BstEII)
5'-G/GTGACC (BstEII in ΔRT-clone)

The restored SmaI recognition site is cleaved
by XmaI (creating a 4 nucleotide 5'-overhang)
and converted to a blunt end by treatment with
DNA polymerase I (Klenow fragment)
Similarly, the BstEII-digested recipient vector
pGEM9-T2 is treated with DNA pol I (Klenow
fragment) prior to digestion with ApaI

GACCCGG ←→ GTGACC

GA<u>CCC</u>gggtgACC (underlined codon is P9 in protease)
There is both a SmaI/XmaI and BstEII at the ΔProRT-junction
"Foreign sequences" at the ΔProRT-junction are represented by
lower case letters

HXB (sequence range: 1800 to 4400)

FIG. 4A

```
                                                               >NspI
                                        >Eam1105I
1800      1810      1820      1830              1840
 *         *         *         *                 *
GGA CCA GCG GCT ACA CTA GAA GAA ATG ATG ACA GCA TGT CAG
 G   P   A   A   T   L   E   E   M   M   T   A   C   Q   GAG POLYPROTEIN
 a___a___a___a___a___a___a___a___a___a___a___a___a___a___

>PpuMI   >EaeI
         1850      1860      1870              1880
          *         *         *                 *
GGA GTA GGA GGA CCC GGC CAT AAG GCA AGA GTT TTG GCT GAA
 G   V   G   G   P   G   H   K   A   R   V   L   A   E   GAG POLYPROTEIN
 a___a___a___a___a___a___a___a___a___a___a___a___a___a___
```

FIG. 4B

```
           1890        1900        1910        1920
            *           *           *           *
      GCA ATG AGC CAA GTA ACA AAT TCA GCT ACC ATA ATG ATG CAG
       A   M   S   Q   V   T   N   S   A   T   I   M   M   Q
       a   a   a  GAG POLYPROTEIN a   a   a   a   a   a   a

>MunI
                                              ———
                                              ———
           1930        1940        1950        1960
            *           *           *           *
      AGA GGC AAT TTT AGG AAC CAA AGA AAG ATT GTT AAG TGT TTC
       R   G   N   F   R   N   Q   R   K   I   V   K   C   F
       a   a   a   a   a  GAG POLYPROTEIN a   a   a   a   a   a
```

FIG. 4C

```
     1970           1980           1990           2000
      *              *              *              *
    AAT TGT GGC AAA GAA GGG CAC ACA GCC AGA AAT TGC AGG GCC              >BanII
     N   C   G   K   E   G   H   T   A   R   N   C   R   A              >ApaI
  __a___a___a___a___GAG POLYPROTEIN_a___a___a___a___a___
                   <-------direct repeat #1------->

>AvrII
>StyI
     2010           2020           2030           2040           2050
      *              *              *              *              *
    CCT AGG AAA AAG GGC TGT TGG AAA TGT GGA AAG GAA GGA CAC
     P   R   K   K   G   C   W   K   C   G   K   E   G   H
  __a___a___a___a___GAG POLYPROTEIN_a___a___a___a___a___
                   <-------direct repeat #2------->
```

FIG. 4D

```
              2060       2070       2080       2090
               *          *          *          *
CAA ATG AAA GAT TGT ACT GAG AGA CAG GCT AAT TTT TTA GGG
 Q   M   K   D   C   T   E   R   Q   A   N   F   L   G
   a       a       a    GAG POLYPROTEIN  a       a       a
                          ------>                            <------

>BglII ——
>BstYI ——

2100       2110       2120       2130
               *          *          *          *
AAG ATC TGG CCT TCC TAC AAG GGA AGG CCA GGG AAT TTT CTT
 K   I   W   P   S   Y   K   G   R   P   G   N   F   L
   a       a       a    GAG POLYPROTEIN  a       a       a          L
                                       ------>

---- RVP5 ------------------------>
```

FIG. 4E

```
                                              >EarI
     2140            2150            2160|           2170
       *               *               *|              *
CAG AGC AGA CCA GAG CCA ACA GCC CCA GAA GAG AGC TTC
 Q   S   R   P   E   P   T   A   P   E   E   S   F     a  a  a
                                                       _____  GAG POLYPROTEIN
 Q   S   R   P   E   P   T   A   P   E   E   S   F     b  b  b
                                                       _____  GAG P6 (52 AA)

2180            2190            2200            2210
       *               *               *               *
AGG TCT GGG GTA GAG ACA ACA ACT CCC CCT CAG AAG CAG GAG
 R   S   G   V   E   T   T   T   P   P   Q   K   Q   E   a  a  a
                                                         _____  GAG POLYPROTEIN
 R   S   G   V   E   T   T   T   P   P   Q   K   Q   E   b  b  b
                                                         _____  GAG P6 (52 AA)
```

FIG. 4F

```
2220      2230          2240              2250          2260
 *         *             *                 *    >Bsu36I   *
CCG ATA GAC AAG GAA CTG TAT CCT TTA ACT TCC CTC AGG TCA
 P   I   D   K   E   L   Y   P   L   T   S   L   R   S     a
     ‾‾‾a‾‾‾       ‾‾‾a‾‾‾  GAG POLYPROTEIN  ‾‾‾a‾‾‾   ‾‾‾a‾‾‾
 P   I   D   K   E   L   Y   P   L   T   S   L   R   S     b
 ‾‾‾b‾‾‾   ‾‾‾b‾‾‾    GAG P6 (52 AA) ‾‾‾b‾‾‾   ‾‾‾b‾‾‾  ‾‾‾b‾‾‾
                                         P   Q   V         c
                                         ‾‾‾c‾‾‾  ‾‾‾c‾‾‾

|------→ΔPro
```

FIG. 4G

```
                                                    >Eam1105I
                                                    —|—
           2270              2280              2290              2300
            *                 *                 *                 *
          CTC TTT GGC AAC GAC CCC TCG TCA CAA TAA AG ATA GGG GGG
           L   F   G   N   D   P   S   S   Q   *
         |_a_____a__|GAG POLYPROTEIN_a____a____a___|
          L   F   G   N   D   P   S   S   Q
         |_b_____b__|GAG P6 (52 AA)__b____b___|
          T   L   W   Q   R   P   L   V   T   I   K   I   G   G
         |_c_____c__|        PROTEASE   c    c    c    c    c    c    |
                              |--→ ΔProRT (Tibotec)

2310              2320              2330              2340
            *                 *                 *                 *
          CAA CTA AAG GAA GCT CTA TTA GAT ACA GGA GCA GAT GAT ACA T
           Q   L   K   E   A   L   L   D   T   G   A   D   D   T
         |_c___c___c___c___c___c__|   PROTEASE   c    c    c    c    c  |
```

FIG. 4H

```
       2350        2360        2370        2380
        *           *           *           *
GTA TTA GAA GAA ATG AGT TTG CCA GGA AGA TGG AAA CCA AAA
 V   L   E   E   M   S   L   P   G   R   W   K   P   K
         c           c   c           c           c   c
                        PROTEASE

>BclI
                                                        ─── ─── ───
       2390        2400        2410        2420
        *           *           *           *
ATG ATA GGG GGA ATT GGA GGT TTT ATC AAA GTA AGA CAG TAT
 M   I   G   G   I   G   G   F   I   K   V   R   Q   Y
             c       c           c           c       c
                        PROTEASE 2430        2440        2450        2460        2470
        *           *           *           *           *
GAT CAG ATA CTC ATA GAA ATC TGT GGA CAT AAA GCT ATA GGT
 D   Q   I   L   I   E   I   C   G   H   K   A   I   G
     c   c   c       c       c       c   c       c
                        PROTEASE                        ↓
```

FIG. 4I

```
                    >PpuMI              >HindII
           2480      2490      |2500              2510
            *         *        |  *                *
ACA GTA TTA GTA GGA CCT ACA CCT GTC AAC ATA ATT GGA AGA
 T   V   L   V   G   P   T   P   V   N   I   I   G   R
 c    c    c    c   |____PROTEASE    c    c    c    c
_____OUT5 ------|------------------------------->

>HindII
   |    2520      2530      2540      2550
   |     *         *          *         *
AAT CTG TTG ACT CAG ATT GGT TGC ACT TTA AAT TTT CCC ATT
 N   L   L   T   Q   I   G   C   T   L   N   F   P   I
 c    c    c    c   |____PROTEASE    c    c    c    c |  D
                                                      <-----
```

FIG. 4J

```
          2560        2570        2580        2590
            *           *           *           *
         AGC CCT ATT GAG ACT GTA CCA GTA AAA TTA AAG CCA GGA ATG
          S   P   I   E   T   V   P   V   K   L   K   P   G   M
              d   d       d   d   REVERSE TRANSCRIPTASE  d   d   d   d
              |-- IN5 -------------->
                  ΔPro ---->|

>MscI
                                        |--|
                                      >EaeI
                                      |----|
          2600        2610        2620        2630
            *           *           *           *
         GAT GGC CCA AAA GTT AAA CAA TGG CCA TTG ACA GAA GAA AAA
          D   G   P   K   V   K   Q   W   P   L   T   E   E   K
          d   d   d           REVERSE TRANSCRIPTASE  d   d   d   d
```

FIG. 4L

```
     2770            2780            2790            2800
      *               *               *               *
AAA TTA GTA GAT TTC AGA GAA CTT AAT AAG AGA ACT CAA GAC
 K   L   V   D   F   R   E   L   N   K   R   T   Q   D
 d___d___d___REVERSE TRANSCRIPTASE___d___d___d___d___d 2810            2820            2830            2840
      *               *               *               *
TTC TGG GAA GTT CAA TTA GGA ATA CCA CAT CCC GCA GGC TTA
 F   W   E   V   Q   L   G   I   P   H   P   A   G   L
 d___d___d___REVERSE TRANSCRIPTASE___d___d___d___d 2850            2860            2870            2880            2890
      *               *               *               *               *
AAA AAG AAA AAA TCA GTA ACA GTA CTG GAT GTG GGT GAT GCA
 K   K   K   K   S   V   T   V   L   D   V   G   D   A
 d___d___d___REVERSE TRANSCRIPTASE___d___d___d___d
```

FIG. 4M

```
                                                                    >Bst1107I
                                                                   ─
                                                                   >AccI
                                                                   ══
                                       2910         2920        ║2930║
        2900                            *            *         ══  *
         *                                                      ║   ║
TAT TTT TCA GTT CCC TTA GAT GAA GAC TTC AGG AAG TAT ACT
 Y   F   S   V   P   L   D   E   D   F   R   K   Y   T
 ───d───d───d──── REVERSE TRANSCRIPTASE ───d───d───d────

2950         2960        2970
        2940              *            *           *
         *
GCA TTT ACC ATA CCT AGT ATA AAC AAT GAG ACA CCA GGG ATT
 A   F   T   I   P   S   I   N   N   E   T   P   G   I
 ───d───d───d──── REVERSE TRANSCRIPTASE ───d───d───d────
```

FIG. 4N

>EcoRV
```
       2980            2990            3000            3010
         *               *               *               *
AGA TAT CAG TAC AAT GTG CTT CCA CAG GGA TGG AAA GGA TCA
 R   Y   Q   Y   N   V   L   P   Q   G   W   K   G   S
 d   d   d   REVERSE TRANSCRIPTASE    d   d   d   d   d

>SspI
       3020            3030            3040            3050
         *               *               *               *
CCA GCA ATA TTC CAA AGT AGC ATG ACA AAA ATC TTA GAG CCT
 P   A   I   F   Q   S   S   M   T   K   I   L   E   P
 d   d   d   d   REVERSE TRANSCRIPTASE    d   d   d   d 3060            3070            3080            3090            3100
         *               *               *               *               *
TTT AGA AAA CAA AAT CCA GAC ATA GTT ATC TAT CAA TAC ATG
 F   R   K   Q   N   P   D   I   V   I   Y   Q   Y   M
 d   d   d   d   REVERSE TRANSCRIPTASE    d   d   d   d
```

FIG. 40

>BstyI

```
          3110              | 3120           3130              3140
           *                |  *              *                 *
GAT GAT TTG TAT GTA GGA TCT GAC TTA GAA ATA GGG CAG CAT
 D   D   L   Y   V   G   S   D   L   E   I   G   Q   H
 d   d   d   REVERSE TRANSCRIPTASE          d   d   d   d 3150           3160           3170              3180
           *              *              *                 *
AGA ACA AAA ATA GAG GAG CTG AGA CAA CAT CTG TTG AGG TGG
 R   T   K   I   E   E   L   R   Q   H   L   L   R   W
 d   d   d   REVERSE TRANSCRIPTASE          d   d   d   d 3190           3200           3210              3220
           *              *              *                 *
GGA CTT ACC ACA CCA GAC AAA AAA CAT CAG AAA GAA CCT CCA
 G   L   T   T   P   D   K   K   H   Q   K   E   P   P
 d   d   d   REVERSE TRANSCRIPTASE          d   d   d   d
```

FIG. 4Q

```
    3660                3370                3380                3390
     *                   *                   *                   *
CAG ATT TAC CCA GGG ATT AAA GTA AGG CAA TTA TGT AAA CTC
 Q   I   Y   P   G   I   K   V   R   Q   L   C   K   L
 d       d       d       REVERSE TRANSCRIPTASE  d   d   d   d 3400                3410                3420                3430
     *                   *                   *                   *
CTT AGA GGA ACC AAA GCA CTA ACA GAA GTA ATA CCA CTA ACA
 L   R   G   T   K   A   L   T   E   V   I   P   L   T
 d   d   d       REVERSE TRANSCRIPTASE  d       d   d   d 3440                3450                3460                3470
     *                   *                   *                   *
GAA GAA GCA GAG CTA GAA CTG GCA GAA AAC AGA GAG ATT CTA
 E   E   A   E   L   E   L   A   E   N   R   E   I   L
     d   d   d       REVERSE TRANSCRIPTASE  d   d   d   d
```

FIG. 4R

>PflMI

```
      3480            3490             3500             3510             3520
       *               *                *                *                *
                   AAA GAA CCA GTA CAT GGA GTG TAT TAT GAC CCA TCA AAA GAC
                    K   E   P   V   H   G   V   Y   Y   D   P   S   K   D
                    d   d           REVERSE TRANSCRIPTASE    d   d   d   d 3530            3540             3550             3560
       *               *                *                *
  TTA ATA GCA GAA ATA CAG AAG CAG GGG CAA GGC CAA TGG ACA
   L   I   A   E   I   Q   K   Q   G   Q   G   Q   W   T
   d   d           REVERSE TRANSCRIPTASE    d   d   d   d 3570            3580             3590             3600
       *               *                *                *
  TAT CAA ATT TAT CAA GAG CCA TTT AAA AAT CTG AAA ACA GGA
   Y   Q   I   Y   Q   E   P   F   K   N   L   K   T   G
   d   d   d       REVERSE TRANSCRIPTASE    d   d   d   d
```

FIG. 4S

```
3610        3620        3630        3640
  *           *           *           *
AAA TAT GCA AGA ATG AGG GGT GCC CAC ACT AAT GAT GTA AAA
 K   Y   A   R   M   R   G   A   H   T   N   D   V   K
     d___d___d___REVERSE TRANSCRIPTASE___d___d___d___d 3650        3660        3670        3680
  *           *           *           *
CAA TTA ACA GAG GCA GTG CAA AAA ATA ACC ACA GAA AGC ATA
 Q   L   T   E   A   V   Q   K   I   T   T   E   S   I
 d___d___d___REVERSE TRANSCRIPTASE___d___d___d___d 3690        3700        3710        3720        3730
  *           *           *           *           *
GTA ATA TGG GGA AAG ACT CCT AAA TTT AAA CTG CCC ATA CAA
 V   I   W   G   K   T   P   K   F   K   L   P   I   Q
     d___d___d___REVERSE TRANSCRIPTASE___d___d___d___d
```

FIG. 4T

```
                    3740                       3750                       3760                       3770
                     *                          *                          *                          *
              AAG GAA ACA TGG GAA ACA TGG TGG ACA GAG TAT TGG CAA GCC
               K   E   T   W   E   T   W   W   T   E   Y   W   Q   A
              d___d___REVERSE TRANSCRIPTASE___d___d___d___

3780                       3790                       3800                       3810
                     *                          *                          *                          *
              ACC TGG ATT CCT GAG TGG GAG TTT GTT AAT ACC CCT CCC TTA
               T   W   I   P   E   W   E   F   V   N   T   P   P   L
              d___d___d___REVERSE TRANSCRIPTASE___d___d___d___

>KpnI
                              |----|
                    3820      3830                       3840                       3850
                     *         *                          *                          *
              GTG AAA TTA TGG TAC CAG TTA GAG AAA GAA CCC ATA GTA GGA
               V   K   L   W   Y   Q   L   E   K   E   P   I   V   G
              d___d___d___REVERSE TRANSCRIPTASE___d___d___d___d___
```

FIG. 4U

```
      3860            3870              3880              3890
       *               *                 *                 *
      GCA GAA ACC TTC TAT GTA GAT GGG GCA GCT AAC AGG GAG ACT
       A   E   T   F   Y   V   D   G   A   A   N   R   E   T
       d   d   d   REVERSE TRANSCRIPTASE     d   d   d   d   d 3900            3910              3920              3930              3940
       *               *                 *                 *                 *
      AAA TTA GGA AAA GCA GGA TAT GTT ACT AAT AGA GGA AGA CAA
       K   L   G   K   A   G   Y   V   T   N   R   G   R   Q
       d   d   d   REVERSE TRANSCRIPTASE     d   d   d   d   d 3950            3960              3970              3980
       *               *                 *                 *
      AAA GTT GTC ACC CTA ACT GAC ACA ACA AAT CAG AAG ACT GAG
       K   V   V   T   L   T   D   T   T   N   Q   K   T   E
       d   d   d   REVERSE TRANSCRIPTASE     d   d   d   d   d
```

FIG. 4V

```
              3990          4000          4010          4020
               *             *             *             *
         TTA CAA GCA ATT TAT CTA GCT TTG CAG GAT TCG GGA TTA GAA
          L   Q   A   I   Y   L   A   L   Q   D   S   G   L   E
          d   d   d    REVERSE TRANSCRIPTASE  d   d   d   d 4030          4040          4050          4060
               *             *             *             *
         GTA AAC ATA GTA ACA GAC TCA CAA TAT GCA TTA GGA ATC ATT
          V   N   I   V   T   D   S   Q   Y   A   L   G   I   I
          d   d   d    REVERSE TRANSCRIPTASE  d   d   d   d 4070          4080          4090          4100
               *             *             *             *
         CAA GCA CAA CCA GAT CAA AGT GAA TCA GAG TTA GTC AAT CAA
          Q   A   Q   P   D   Q   S   E   S   E   L   V   N   Q
          d   d   d    REVERSE TRANSCRIPTASE  d   d   d   d
```

FIG. 4W

```
       4110           4120           4130           4140           4150
        *              *              *              *              *
ATA ATA GAG CAG TTA ATA AAA AAG GAA AAG GTC TAT CTG GCA
 I   I   E   Q   L   I   K   K   E   K   V   Y   L   A
____d___d___d___ REVERSE TRANSCRIPTASE___d___d___d___d___
     |ΔRT    --->|
ΔProRT(Tibotec) --->|

>KpnI
       |4160          4170           4180           4190
       |*              *              *              *
TGG GTA CCA GCA CAC AAA GGA ATT GGA GGA AAT GAA CAA GTA
 W   V   P   A   H   K   G   I   G   G   N   E   Q   V
___d___d___d___ REVERSE TRANSCRIPTASE___d___d___d___d___
```

FIG. 4X

```
         4200         4210         4220         4230
           *            *            *            *
         GAT AAA TTA GTC AGT GCT GGA ATC AGG AAA GTA CTA TTT TTA
          D   K   L   V   S   A   G   I   R   K   V   L   F   L
         __d___d___d___REVERSE TRANSCRIPTASE___d___d___d___d__
                                              <---------------- IN3 ----

4240         4250         4260         4270         4280
           *            *            *            *            *
         GATGGA ATAGATAAGG CCCAAGATGA ACATGAGAAA TATCACAGTA
         ------------->                         <-------------- OUT3 ---

BspMI
                                              |---|
         4290         4300         4310         4320         4330
           *            *            *            *            *
         ATTGGAGAGC AATGGCTAGT GATTTTAACC TGCCACCTGT AGTAGCAAAA
         ------------->
```

FIG. 4Y

```
          >PvuII
          |     |
     4340 |     | 4350      4360       4370       4380
        *       *          *          *          *
GAAATAGTAG CCAGCTGTGA TAAATGTCAG CTAAAAGGAG AAGCCATGCA

>AccI
  |
  | 4390      4400
  *          *
TGGACAAGTA GACTGTAGTC
```

METHOD OF MANAGING THE CHEMOTHERAPY OF PATIENTS WHO ARE HIV POSITIVE BASED ON THE PHENOTYPIC DRUG SENSITIVITY OF HUMAN HIV STRAINS

This application is a divisional application of application Ser. No. 09/117,217, filed Jul. 24, 1998, now U.S. Pat. No. 6,221,578, which is a §371 application of PCT International Application No. PCT/IB97/00071 filed Jan. 24, 1997. The entire contents of these applications are hereby incorporated by reference.

TECHNICAL FIELD

The present invention relates to a method of managing the chemotherapy of patients who are HIV positive, as well as a clinical management device for use by physicians treating such patients based on the phenotypic drug sensitivity of human HIV strains for inhibitors of one or more enzymes of the pol gene of HIV, as well as a method for simultaneously determining the phenotypic drug sensitivity of two or more of the enzymes of the pol gene of HIV to inhibitors thereof.

BACKGROUND ART

To date, several chemotherapeutic regimens have been developed for treating HIV infected patients. Certain of these regimens have been approved for clinical use, and others are the subject of on-going clinical trials. It can be assumed that the number of approved chemotherapeutic regimens will increase steadily in the near future. Increasingly, combination therapy or multiple drug treatment regimens are being used because of the development of drug-resistant HIV variants during therapy. Although these chemotherapeutic regimens have been shown to exert an effect on virological (viral load), immunological and clinical parameters of HIV disease, practical experience teaches that these effects are transient. In particular, one finds that the HIV strains infecting an individual patient after a while start to display reduced sensitivity to the drug or drug combination with which said patient is being treated. The loss of efficacy of the chemotherapy can vary from patient to patient, from drug to drug, or from drug combination to drug combination. It is well established that the loss of efficacy to a particular type of chemotherapy can be associated with a genotypic pattern of amino acid changes in the genome of the HIV strains infecting the patient. This probably renders these HIV strains less susceptible to the chemotherapy. As an HIV infected patient is exposed to several chemotherapeutic regimens over extended periods of time, more complex patterns of amino acid changes in the genome of infecting HIV strains occur which for the present defeat a rational approach to the further treatment of the infected patient. As implied in the previous explanation, one can routinely determine the genotypic changes occurring in HIV strains exposed to different chemotherapeutic regimens involving single or multiple anti-HIV drugs, but thus far it has proven very difficult to derive from these data information enabling a physician in charge of prescribing the chemotherapy whether or not it is sensible to initiate or continue a particular chemotherapeutic regimen. In other words, the genotypic information which is available on a limited scale, cannot routinely be translated into phenotypic information enabling the responsible physician to make the crucial decision as to which chemotherapy a patient should preferably follow. The problem also exists for drug-naive patients who become infected by drug-resistant HIV strains.

Viral load monitoring is becoming a routine aspect of HIV care. However, viral load number alone cannot be used as a basis for deciding which drugs to use alone or in combination.

Combination therapy is becoming increasingly the chemotherapeutic regimen of choice. When a person using a combination of drugs begins to experience drug failure, it is impossible to know with certainty which of the drugs in the combination is no longer active. One cannot simply replace all of the drugs, because of the limited number of drugs currently available. Furthermore, if one replaces an entire chemotherapeutic regimen, one may discard one or more drugs which are active for that particular patient. Furthermore, it is possible for viruses which display resistance to a particular inhibitor to also display varying degrees of cross-resistance to other inhibitors.

Ideally, therefore, every time a person has a viral load test and a viral load increase is detected, a drug sensitivity/resistance test should also be carried out. Until effective curative therapy is developed, management of HIV disease will require such testing.

Currently there does exist a phenotyping method which is based on virus isolation from plasma in the presence of donor peripheral blood mononuclear cells (PBMCs), and subsequent phenotyping in said cells (Japour, A. J., et al. (1993) Antimicrobial Agents and Chemotherapy; Vol. 37, No. 5, p1095–1101). This co-cultivation method, which is advocated by the AIDS Clinical Trial Group (ACTG)—particularly for phenotyping AZT (synonymous herein with zidovudine/Retrovir (Retrovir is a Trade Mark)) resistance, is time-consuming, costly and too complex to be used on a routine basis.

A phenotypic recombinant virus assay for assessment of drug susceptibility of HIV Type 1 isolates to reverse transcriptase (RT) inhibitors has been developed by Kellam, P. and Larder, B. A. (Antimicrobial Agents and Chemotherapy (1994) Vol. 38, No. 1, p23–30). This procedure allows the generation of viable virus by homologous recombination of a PCR-derived pool of RT coding sequences into an RT-deleted, noninfectious proviral clone, pHIVΔRTBstEII. Analysis of two patients during the course of zidovudine therapy showed that this approach produced viruses which accurately exhibited the same genotype and phenotype as that of the original infected PBL DNA. However, the procedure involves isolation of the patient virus by co-cultivation of patient plasma or patient PBMCs with donor PBMCs. Such prior cultivation of virus may distort the original virus composition. Furthermore, this method, although allowing one to determine the sensitivity of the isolates to various inhibitors, does not provide the physician with information as to whether to continue with the existing chemotherapeutic regimen or to alter the therapy.

Also when one enzyme only of the pol gene is being studied, the method does not readily lend itself to routine phenotypic assessment of combination therapy which conventionally involves the use of one protease and 2 RT inhibitors.

The nested PCR (polymerase chain reaction) procedure used in ti recombinant virus assay can lead to a situation where the recombinant virus does not truly reflect the situation with the HIV strains infecting the patient under investigation. This problem resides in DNA sequence homology and the minimum amount of homology required for homologous recombination in mammalian cells (C. Rubnitz, J. and Subramini, S. (1984) Molecular and Cellular Biology Vol. 4, No. 11, p2253–2258). Accordingly, any phenotypic assay based on the recombinant virus approach should endeavour to ensure that as much as possible of the patient material is amplified and that there is maximum recombination.

Thus, the RNA extraction and nested PCR procedures employed should ensure that the viral genetic material is amplified such that the amplified material maximally reflects the viral genetic diversity in the patient being investigated.

In current clinical practice there is therefore a hard-felt need (a) to determine rapidly and on a routine basis the phenotypic drug sensitivity of HIV strains infecting a particular patient, (b) to process the thus obtained data into easily understood information, and (c) to initiate, continue or adjust on the basis of said information the chemotherapy prescribed for said particular patients.

DISCLOSURE OF THE INVENTION

According to a first aspect of the invention there is provided a method of managing HIV chemotherapy of patients who are HIV positive, which comprises transfecting a cell line susceptible to infection by HIV with a sequence from the pol gene of HIV, obtained by isolating viral RNA from a sample of a biological material from a patient and reverse transcribing the desired region of said pol gene, and a HIV-DNA construct from which said sequence has been deleted, culturing said transfected cells so as to create a stock of chimeric viruses providing an indication of the resistance profile of the circulating virus, assessing the phenotypic sensitivity of said chimeric viruses to an inhibitor of said enzyme encoded by the pol gene of HIV and assigning a value thereto constructing a data set comprising said value for chimeric virus sensitivity and the corresponding value for a chimeric wild-type strain HIV, repeating the sensitivity assessment for at least two further inhibitors and thereby constructing at least three such data sets in total, representing said data sets in two dimensional or three dimensional graphical form such that the difference between the chimeric and wild-type sensitivities in the case of each data set provides a visual measure the resistance of the chimeric stock to treatment by the inhibitor in question, and selecting the optimum inhibitor(s) on the basis of the graphical representation of the resistances so measured.

The method according to the invention yields phenotypic information on individual HIV infected patients on a large scale, economically and rapidly. The method is applicable to all currently available chemotherapeutic regimens and it is expected to be equally applicable to future chemotherapeutic regimens.

The method according to the invention provides the physician with phenotypic data on patient HIV strains which can be immediately used to determine whether a particular chemotherapeutic regimen should be initiated, continued or adjusted.

Preferably, the data sets are represented on a polygonal or quasi-circular graph comprising:
(a) a plurality of normalised axes extending radially from an origin, each axis corresponding to one data set or inhibitor or combination thereof;
(b) the axes being normalised such that the sensitivity values for wild-type HIV for the various inhibitors are equal on each axis, the data points for wild-type HIV being optionally represented and connected to form a regular polygon whose vertices lie on the axes and whose center is defined by the origin;
(c) on each axis a data point representing the sensitivity value of the chimeric HIV stock against the inhibitor corresponding to said axis is plotted, the chimeric data points being optionally connected to form a regular or irregular polygon the shape of which represents the resistance of the chimeric stock to a range of inhibitors.

A polygonal or quasi-circular graph provides the advantage that the patient's resistance to a number of drugs is characterised in terms of the degree of divergence between the polygon representing the patient's chimeric HIV stock and the polygon representing the wild-type strain. The areas of the polygons will generally diverge more in some areas than in others, indicating in each case a greater or lesser degree of resistance to the inhibitor whose axis passes through the area in question.

Thus, the method according to the invention takes a chimeric HIV stock and provides a map of the resistance of this stock across a range of inhibitors. In this way the map or graph provides a technical characterisation of an aspect of the chimeric stock which is not obtained by conventional measurements.

In a preferred embodiment, the normalised axes are equiangular from one another.

Further, preferably, each axis has a logarithmic scale.

Further, preferably, eccentric data points in the chimeric polygon, if represented, identify inhibitors whose usefulness can be assumed to be of little or no benefit to the patient, while data points lying within, on or close outside the wild-type polygon identify inhibitors whose usefulness can be assumed to be of substantial benefit to the patient.

When worst case values are represented along with the chimeric and wild-type HIV, a usually irregular polygon encloses the chimeric and wild-type polygons. The meaning of the term "eccentric" as used above denotes a data point lying relatively close to the worst-case border and relatively far from the wild-type polygon. Similarly the term "close outside the wild-type polygon" refers to relative closeness to the wild-type polygon when compared to the distance from the worst-case border.

The method as hereinabove defined is limited in the sense that the measurable resistance against an inhibitor is dependent on the particular range of concentrations of the inhibitor used. Also one must endeavour to reduce the effects of biological variability. Accordingly, it is desirable to obtain a value for maximum or worst-case measurable resistance where it is assumed that a given inhibitor has no effect. This concentration, e.g. 100 $\mu$M, is generally the maximum concentration that can practically be tested, but may also be derived from e.g. pharmacological, toxicological or pharmacokinetic studies. The comparison of the resistance level of the patient under investigation and the maximum measurable resistance determines what is the significant level of resistance for the patient under investigation. The maximum measurable resistance and the actual resistance can be suitably shown on a bar graph as hereinafter described.

In a still further preferred embodiment of the invention each of said three or more data sets further comprises a value for worst-case measurable resistance for the inhibitor in question, said worst case values being represented on said graphical representations such that the data point for the chimeric stock can be compared both to wild-type and to worst-case HIV, thereby providing an assessment of the relative value of the inhibitor in a particular case.

Experiments with in excess of 150 patient samples have revealed a close correlation between resistance development and therapy history as hereinafter further illustrated in the Examples. A close correlation has been found with the data generated in accordance with the invention relative to classical virus isolation and phenotyping techniques.

The method in accordance with the invention can thus be used for an individualised and more rational management of HIV chemotherapy. Thus, use of the method according to the invention in combination with the proper administration of anti-HIV drugs should ultimately lead to better treatment and survival of patients infected with the HIV virus.

The method according to the invention has particular application where an individual patient has been receiving many different drugs and his mutation pattern is not readily interpreted by attending physicians.

According to a further aspect of the invention there is provided a method of managing HIV chemotherapy of patients who are HIV positive, which comprises the steps of:
(a) periodically assessing the phenotypic sensitivity of a patient's HIV strains by a method hereinabove described;
(b) maintaining the chemotherapy with the selected inhibitor while the patient's HIV strains remain susceptible to the selected chemotherapy;
(c) selecting a different inhibitor if and when the susceptibility of the original inhibitor decreases.

According to a still further aspect of the invention there is provided a clinical management device for use in the management of chemotherapy of patients who are HIV positive, said device bearing a graphical representation of a plurality of data sets as hereinabove defined.

We have coined the term "Antivirogram" for the clinical management device according to the invention and this term will be used hereinafter in the specification. This device provides the physician with a clear representation of the relative changes and susceptibilities for different inhibitors which are or which may be used in the clinical management of individual HIV-infected patients.

By HIV herein is generally meant HIV-1. However, the invention is also applicable to HIV-2.

Preferably, the phenotypic sensitivity of said chimeric viruses to inhibitors of at least two enzymes encoded by the pol gene of HIV is simultaneously assessed.

In a further aspect of the invention there is provided a method of determining the phenotypic drug sensitivity of individual HIV strains in a patient to inhibitors of at least two enzymes encoded by the pol gene o HIV, which comprises transfecting a cell line susceptible to infection by HIV with a sequence from the pol gene of HIV, obtained by isolating viral RNA from a sample of a biological material from a patient and reverse transcribing the desired region of said pol gene, and a HIV-DNA construct from which said sequence has been deleted, culturing said transfected cells so as to create a stock of chimeric viruses providing an indication of the resistance profile of the circulating virus and assessing the phenotypic sensitivity of said chimeric viruses to inhibitors of said enzymes encoded by the pol gene of HIV.

The desired sequence from the pol gene is isolated from a sample of a biological material obtained from the patient whose phenotypic drug sensitivity is being determined. A wide variety of biological materials can be used for the isolation of the desired sequence.

Thus, the biological material can be selected from plasma, serum or a cell-free body fluid selected from semen and vaginal fluid. Plasma is particularly preferred and is particularly advantageous relative to the use of PBMCs as used in the prior art described above.

Alternatively, the biological material can be whole blood to which an RNA stabiliser has been added.

In a still further embodiment, the biological material can be a solid tissue material selected from brain tissue or lymph nodal tissue, or other tissue obtained by biopsy.

As hereinafter demonstrated, when a biological material such as plasma is used in the isolation of the desired sequence, a minimal volume of plasma can be used, typically about 100–250 $\mu l$, more particularly of the order of 200 $\mu l$.

Further, preferably the two enzymes selected will be selected from HIV RT, protease and integrase.

Viral RNA is conveniently isolated in accordance with the invention by methods known per se, for example the method of Boom, R. et al. (Journal of Clinical Microbiology (1990) Vol. 28, No. 3, p.495–503).

In the case of plasma, serum and cell-free body fluids, one can also use the QIAamp viral RNA kit marketed by the Qiagen group of companies.

Preferably, the cell line susceptible to infection by HIV is a $CD4^+$ T-cell line.

Further, preferably, the $CD4^+$ T-cell line is the MT4 cell line or the HeLa $CD4^+$ cell line.

Reverse transcription can be carried out with a commercial kit such as the GeneAmp Reverse Transcriptase Kit marketed by Perkin Elmer.

The desired region of the patient pol gene is preferably reverse transcribed using a specific downstream primer.

In the case where the sequence to be reverse transcribed is that coding for reverse transcriptase or reverse transcriptase and protease, the downstream primer is preferably OUT3: 5'-CAT TGC TCT CCA ATT ACT GTG ATA TTT CTC ATG-3' (SEQ ID NO: 1).

In a particularly preferred embodiment a patient's HIV RT gene and HIV protease gene are reverse transcribed using the HIV-1 specific OUT 3 primer and a genetically engineered reverse transcriptase lacking RNase H activity, such that the total RNA to be transcribed is converted to cDNA without being degraded. Such a genetically engineered reverse transcriptase, the Expand (Expand is a Trade Mark) reverse transcriptase, can be obtained from Boehringer Mannheim GmbH.

Expand reverse transcriptase is a RNA directed DNA polymerase. The enzyme is a genetically engineered version of the Moloney Murine Leukaemia Virus reverse transcriptase (M-MuLV-RT). Point mutation within the RNase H sequence reduces the RNase H activity to below the detectable level. Using this genetically engineered reverse transcriptase enables one to obtain higher amounts of full length cDNA transcripts.

Following reverse transcription the transcribed DNA is amplified using the technique of PCR.

Preferably, the product of reverse transcription is amplified using a nested PCR technique.

Preferably, in the case where the region of interest is the RT region, a nested PCR technique is used using inner and outer primers as described by Kellam, P. and Larder, B. A. (1994 supra). When the region of interest is that spanning the RT and protease genes, the specific primers used are preferably a combination of OUT 3/IN 3 (downstream) and RVP 5 (upstream).

The primer RVP 5 (Maschera, B., et al. Journal of Virology, 69, 5431–5436) has the sequence 5'-GGGAAGATCTGGCC TTCCTACAAGGG-3' (SEQ ID NO: 2).

A schematic representation of the amplification is set forth in FIG. 3 and is described in greater detail in Example 2.

The amplification of the protease cDNA actually involves a hemi-nested PCR procedure as will be apparent from FIG. 3.

The nested PCR technique has the advantage over the known simple PCR techniques in that it enables one to obtain the most specific PCR product.

However, to obtain an even higher fidelity and yield during PCR, one can make use of a mixture of thermostable polymerases (Barnes, W. M. (1994) Proc. Natl. Acad. Sci. U.S.A. 91, 2216–2220). Such a polymerase mixture is available from Boehringer Mannheim GmbH, namely the Expand (Expand is a Trade Mark) high fidelity PCR system. Using this system we have obtained increased sensitivity, namely a sensitivity which is ten times or greater than that obtained with a conventional PCR procedure using Taq polymerase alone.

When the region of the pol gene is that embracing the RT and protease genes, preferably the HIV-DNA construct is one from which the RT and protease genes are deleted and is the plasmid pGEMT3-ΔPRT as deposited at the Belgian Coordinated Collections of Microorganisms-BCCM LMBP-Collection on Nov. 8, 1996 under the number LMBP3590.

However, several approaches can be adopted to generate a plasmid containing the HIV-1 provirus carrying a deletion for the protease as well as for the RT gene. One possibility is the introduction of the desired deletion by means of oligonucleotide-mediated mutagenesis. However, the procedure adopted hereinafter in Example 2 involves the generation of the desired construct by making use of specific restriction enzymes and subcloning procedures, as hereinafter described. Although the final results depend on the available restriction sites a major advantage of this procedure is that one can obtain conclusive results rapidly.

To ensure the most efficient outcome for the transfection, the PCR-product, being transfected, should ideally be purified by anion exchange spin columns in a manner known per se. A suitable kit is the QIAquick PCR Purification Kit marketed by the Qiagen group of companies.

Transfection can be achieved by electroporation or, alternatively, by the use of lipids, especially cathionic lipids, DEAE dextran, $CaHPO_4$, etc.

In the case of lipid transfection one can avail of a PERFECT (PERFECT is a Trade Mark) transfection kit marketed by Invitrogen B.V. of Leek, the Netherlands.

Thus, for transfection an HIV-DNA construct from which the gene or genes of choice from the pol gene has/have been deleted is used in conjunction with the product obtained following amplification.

The construct can be the plasmid pHIVΔRT (obtainable from the Medical Research Council (MRC)) if it is the RT gene only that is deleted. When the RT and protease genes are both deleted a suitable HIV DNA construct is the plasmid pGEMT3-ΔPRT described herein and which is a high copy vector. Such plasmids are linearised prior to transfection according to methods known per se.

A particular advantage of using a construct coding for more than one pol gene enzyme, for example a ΔPRT construct, is that one is more likely to include more of the original patient material in the construct than if a single gene is used, so that the amplified material reflects to a greater extent the viral genetic diversity in the particular patient being investigated.

It will be appreciated that it is preferable that the specific primers selected for the nested PCR are located outside the body sequences of the target enzymes to be amplified and investigated. It will furthermore be appreciated that a combination of RT and protease is likely to provide better results for studying RT than RT alone, because forty more amino acids are patient borne relative to the situation with RT alone. For studying the protease, one should be aware that the first nine amino acids of the protease are still derived from the construct's (pGEMT3-ΔPRT) wild-type backbone.

When the transfection of the cells is achieved through electroporation, the parameters selected are optimized to achieve good cell growth and virus production. The electroporation can convenient be conducted at approximately 250 μF and 300 V. Preferably, the electroporation is conducted in the presence of about 10 μg of linearise plasmid e.g. pHIVΔRTBstEII and about 5 μg of amplified PCR produc e.g. RT PCR product. Upon successful intracellular homologous recombination, new chimeric HIV is formed within 5 to 10 days. With known techniques typical cultivation times are 12–14 days before chimeric HIV is formed. Culture supernatant aliquots are stored at −70° C. or lower temperatures.

It is readily seen that one can use the above methods for isolating and amplifying other HIV genes, e.g. the integrase gene, or more than one other HIV gene, e.g. both the RT and the integrase gene, and transfecting a $CD4^+$ T-cell with the respective integrase or RT/integrase PCR products in conjunction with an appropriate linearised HIV-DNA construct from which the relevant gene (or genes) is deleted.

The newly formed chimeric viruses are titrated and then analysed for their phenotypic sensitivity (i.e. susceptibility) to the different pol gene enzyme inhibitors, preferably in an automated cell-based assay.

Preferably, the phenotypic drug sensitivity of the chimeric viruses and of the wild HIV strain, which is suitably a recombinant wild HIV strain, to one or more RT, protease or integrase inhibitor(s) is expressed as an inhibitory concentration (IC value).

The susceptibilites of the chimeric viruses and of the wild type HIV strain to one or more RT inhibitors and/or one or more protease inhibitors and/or one or more integrase inhibitors can be expressed as for example 50% or 90% inhibitory concentrations ($IC_{50}$ or $IC_{90}$ values).

Preferably, RT inhibitors are selected from nucleoside RT inhibitors such as AZT, ddI (didanosinen/Videx (Videx is a Trade Mark), ddC (zalcitabine), 3TC (lamivudine), d4T (stavudine), non-nucleoside RT inhibitors such as delavirdine (U 9051125 (BMAP)/Rescriptor (Rescriptor is a Trade Mark)), loviride (alpha-APA), nevirapine (B1-RG-587/Viramune (Viramune is a Trade Mark) and tivirapine (8-Cl-TIBO(R86183)), protease inhibitors such as saquinavir, indinavir and ritonavir and integrase inhibitors such as caffeic acid phenylethyl ester (CAPE).

Suitable RT and/or protease inhibitors and/or integrase inhibitors are selected from nucleoside RT inhibitors such as AZT, ddI, ddC, 3TC, d4T, 1592U89 and the like, non-nucleoside RT inhibitors such as loviride, nevirapine, delaviridine, ateviridine, and tivirapine (8-Cl TIBO) and the like, protease inhibitors such as saquinavir, indinavir and ritonavir and the like, and integrase inhibitors such as caffeic acid phenylethyl ester (CAPE) and HIV integrase inhibitors of the type described in WO 95/08540 and GB 2,271,566.

The method according to the invention comprises the step of comparing the phenotypic drug sensitivity of patient HIV strains with one or more RT inhibitors and/or one or more protease inhibitors, and/or one or more integrase inhibitors to that of a wild type HIV strain. For an easy-to-understand representation of the relative changes in susceptibility to the different drug compounds (or combinations) tested, an Antivirogram graph, is constructed.

The graph should be interpreted as follows: eccentric data points in the antivirogram identify chemotherapeutic regimens unlikely to benefit the HIV infected patient any further, whereas data points within or on the reference polygon, or only slightly beyond the reference polygon, identify chemotherapeutic regimens likely to benefit the HIV infected patient.

The methods according to the invention in combination with the administration of the correct anti-HIV drugs should ultimately lead to better treatment, improved quality of life and improved survival of HIV infected patients; i.e. ineffective treatment (due to the presence of or emergence of resistant HIV strains) can be prevented or halted, and effective chemotherapy can be initiated in good time.

The present invention also concerns a clinical management device for use by physicians treating HIV infected patients comprising an Antivirogram obtainable by the methods hereinbefore described.

BRIEF DESCRIPTION OF THE DRAWINGS

FIG. 1 is a schematic representation of the construction of the plasmid pGEMT3-APRBRT;

FIG. 2 is a further and complementary schematic representation of the construction of the plasmid pGEMT3-ΔPRT comprising SEQ ID NO: 15;

Figure 3:
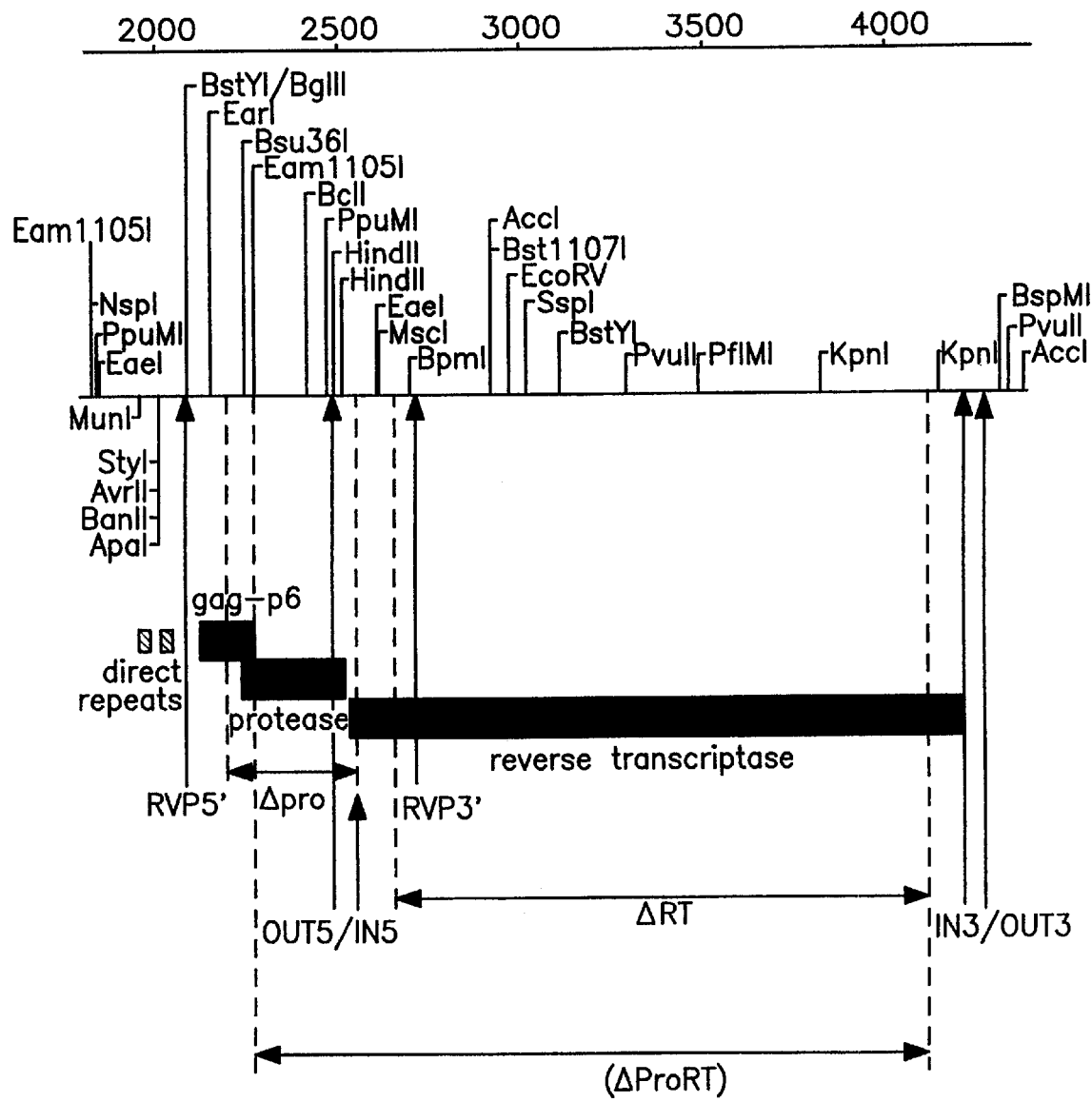
FIG. 3 is a schematic representation of that part of the HIV-HXB2D sequence containing protease and RT genes (SEC ID NOS:7–14)

The invention will be further illustrated by the following Examples.

MODES FOR CARRYING OUT THE INVENTION

EXAMPLE 1 Protocol

1. Extraction and amplification of viral RNA.

RNA was isolated from 100 $\mu$l of plasma according to the method described by Boom, R. et al. (1990, supra), and was reverse transcribed with the GeneAmp reverse transcriptase kit (Perkin Elmer) as described by the manufacturer and using an HIV-1 specific downstream primer (OUT3: 5'-CAT TGC TCT CCA ATT ACT GTG ATA TTT CTC ATC-3'; SEQ ID NO: 1). PCR on reverse transcribed RNA was performed with inner and outer primers as described by Kellam, P. and Larder, B. A. (1994, supra). After chloroform extraction and centrifugation on Centricon 100 columns or centrifugation on anion-exchange spin columns (Quiagen), the isolated PCR product was ready for use in the transfection reactions.

2. Production and isolation of plasmid.

Production of pHIVΔRT (MCR) plasmid was performed in E. coli. Plasmid DNA was isolated from overnight cultures making use of Qiagen columns as described by the manufacturer. Yield of the isolated plasmid was determined spectrophotometrically by A260/280 measurement (optical density measurement at $\lambda$=260 and 280 nm). About 250 $\mu$g of ultrapure plasmid DNA was obtained from 500 ml of bacterial culture. The identity of the isolated plasmid was confirmed by restriction analysis. Subsequently, the isolated plasmid DNA was linearised with BstEII and purified again by a classical phenol/chloroform extraction.

3. Transfection of cells.

MT4 cells were subcultured at a density of 250,000 cells/ml before transfection (exponential growth phase). Cells were pelleted and resuspended in phosphate buffered saline (PBS) at a concentration of 3.1 10E6 cells/ml. A 0.8 ml portion (2.5 10E6 cells/ml) was used for each transfection. Transfection was performed with the Bio-Rad Gene pulser making use of 0.4 cm electrode cuvettes. Cells were electroporated in the presence of 10 g of linearised pHIVΔRT plasmid and approximately 5 $\mu$g of RT PCR product at 250SF and 300 V, followed by a 30-min incubation at room temperature. Subsequently, 10 ml of fresh culture medium was added to the cell suspension and incubation was performed at 37° C. in a humidified atmosphere of 5% $CO_2$.

4. Culture and follow-up of transfected cells.

During 7 to 10 days following the transfection, cells were monitored for the appearance of cytopathogenic effect (CPE). In the absence thereof, cells were subcultured in different flasks. Subsequently, culture supernatants of transfected cells were used to create a stock of recombinant virus and stored in 1.5 ml aliquots at −70° C.

5. Analysis of recombinant virus from patient viral RNA.

After titration of the new viruses, the stocks were used for antiviral experiments in the presence of serial dilutions of different HIV inhibitors. Titres of the harvested supernatants were determined by limited serial dilution titration of virus in MT4 cells.

Viruses with a useful titre were used in antiviral experiments. For this purpose, 96-well microtitre plates were filled with 100$\mu$l of complete culture medium. Subsequently, stock solutions of compounds were added in 25 $\mu$l volumes to series of duplicate wells. HIV- and mock-infected cell samples were included for each drug (or drug combination). Exponentially growing MT4 cells were then transferred to the microtitre plates at a density of 150,000 cells/ml. The cell cultures were then incubated at 37° C. in a humidified atmosphere of 5% $CO_2$. Five days after infection, the viability of the mock- and HIV-infected cells was examined spectrophotometrically by the M1T method (Pauwels, R. et al. J. Virol. Meth. (1988), 20: 309–321) as described in Section 6 below.

6. MTT assay.

To each well of the microtiter plates, 20 $\mu$l of a solution of MTT (7.5 mg/ml in PBS) was added. The plates were further incubated at 37° C. for 1 h. Then, 150 μl of medium was removed without disturbing the MT4 cell clusters containing the formazan crystals. Solubilization of the formazan crystals was achieved by adding 100 μl 5% Triton X-100 in acidified isopropanol (5 ml concentrated HCl per liter solvent). Complete dissolution of the formazan crystals was obtained after the plates had been placed on a plate shaker for 10 min. Finally the absorbances were read at two wavelengths (540 and 690 nm). From these optical density (OD) data, 50% inhibitory ($IC_{50}$) and 50% cytotoxic ($CC_{50}$) concentrations were derived.

EXAMPLE 2

Construction of a pHIVΔRTBstEII-variant with deletion of the HIV-1 protease and reverse transcriptase gene.

The protocol described in Example 1 was repeated, except that the sequence of the HIV pol gene of interest was that coding for RT and protease and the construct prepared was pGEMT3-ΔPRT as described below. Other modifications relative to the procedure set out in Example 1 are set out below.

For amplification of viral RNA, reverse transcription from RNA to DNA was again carried out with the OUT3 primer. However, for the nested PCR procedure the primers used are as shown in FIG. 3. Thus, it will be observed that the nested PCR procedure uses as outer primers RVP5 and OUT3 and as inner primers RVP5 and IN3. Thus, this nested procedure is, in effect a hemi-nested PCR procedure.

Production and isolation of pGEMT3-ΔPRT.

The final pGEMT3-ΔPRT construct is a derivative of pGEM9-Zf(−) (Promega).

In short, the pGEMT3-ΔPRT construct is built up by introducing the desired insert HIV-HXB2 (a protease and reverse transcriptase-deleted proviral HIV-1 clone, including flanking human sequences) into the XbaI restriction site of the vector pGEM9-Zf(−). The proviral genome has been deleted from the AhdI site within the protease gene (surrounding amino acid 9) to the BstEII site of the pHIVΔRTBstEII construct (MRC Repository reference: ADB231). At the junction of the ΔProRT deletion SmaI and BstEII sites are located which can be used for linearisation of the proviral construct prior to transfection. The construction of pGEMT3-ΔPRT is schematically represented in FIGS. 1 and 2. The yield of pGEMT3-ΔPRT was about 1 mg out of 500 ml bacterial culture.

As indicated above, the plasmid pGEMT3-Δ-PRT was deposited at the Belgian Coordinated Collections of Microorganisms-BCCM LMBP-Collection on Nov. 8, 1996 under the number LMBP3590.

It was not expected that the introduction of the proviral genome into another vector (pGEM9-Zf(−) instead of pIB120) would cause major problems. pIB1120, a derivative of pEMBL8(−) (according to information provided by Kodak Scientific Imaging Systems), and pGEM9-ZF(−) are similar vectors. Nevertheless the proviral vector pIB120HIV may be unstable in recA+*E. coli* host cells (Maschera, B., et al. J. Virol. (1995) 69, 5431–5436. Therefore the stability of the pGEMT3-ΔPRT construct should be verified after every new preparation of plasmid.

Figure 4K:
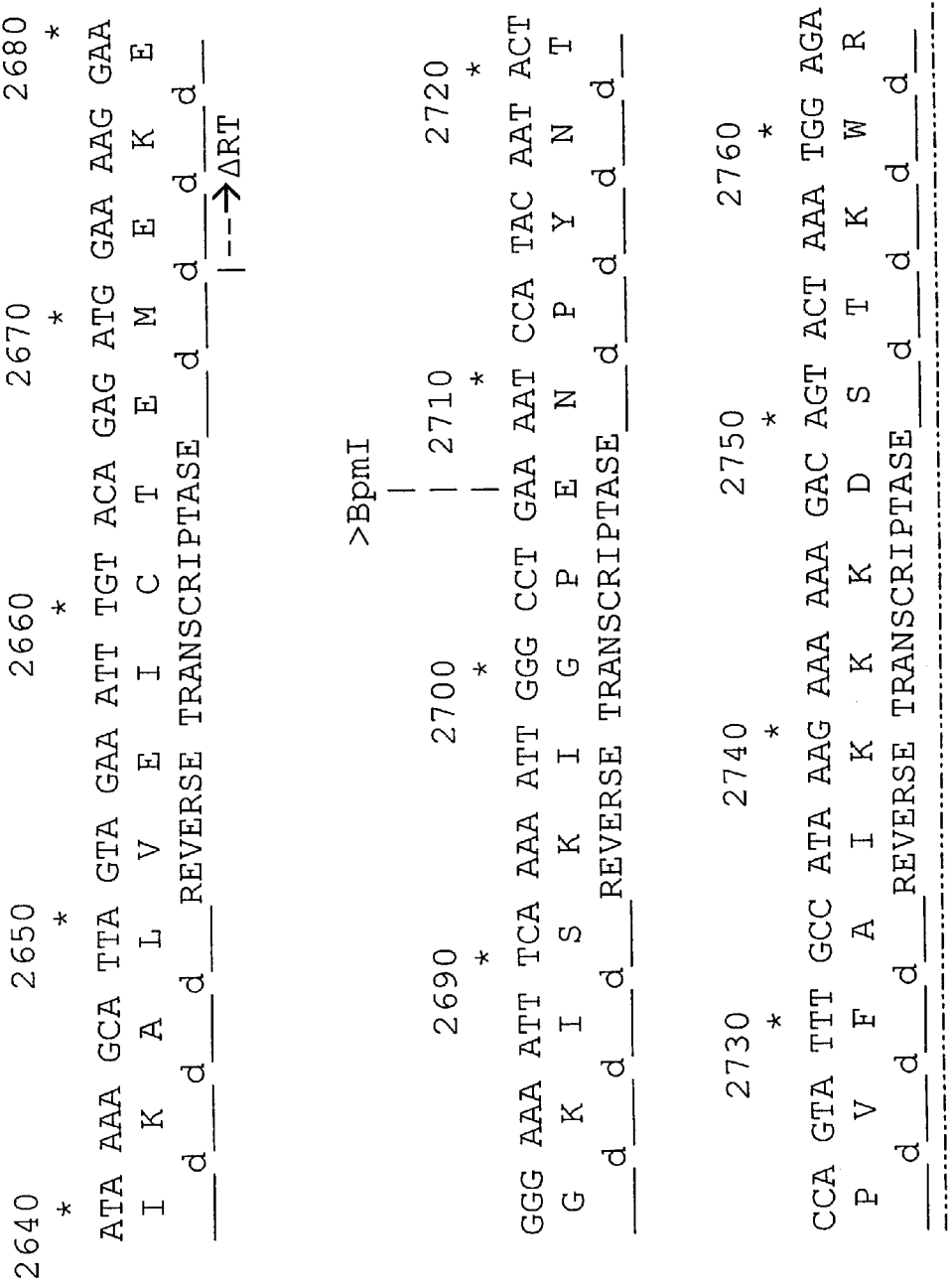
FIG. 4A–H is a complete sequence for that part of the HIV-HXB2D sequence containing protease and RT genes.
Figure 4P:
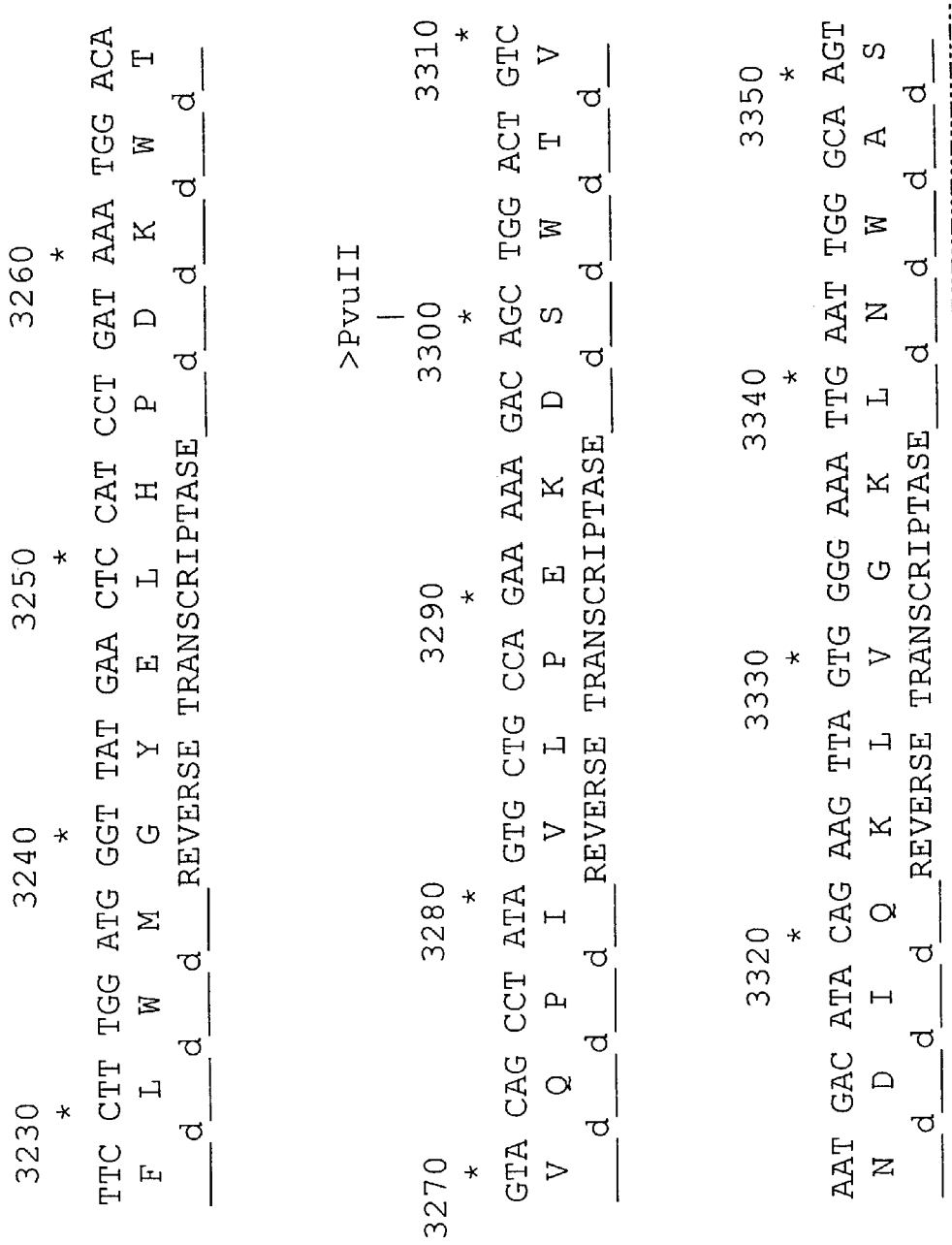

HIV-HXB2 sequence:

The region of interest within the HIV-HXB2D sequence (nucleotide 1800 to 4400) is represented in FIG. 3 (schematically) and FIG. 4 (complete sequence). The location of several genes, restriction sites, primers and deletions (ΔPro, ΔRT, ΔProRT) are also indicated.

The sequence of HIV-1 (isolate HXB2, reference genome, 9718bp) was obtained from the National Center for Biotechnology Information (NCBI), National Library of Medicine, National Institutes of Health via the ENTREZ Document Retrieval System.

Genbank name: HIVHXB2CG

Genbank Accesion No: Ø3455

NCBI Seq.ID No: 327742

Regions of recombination:

In combination with RT-PCR fragments generated by RVP5 and OUT3/IN3 primers, the pGEMT3-ΔPRT vector can be used to transfect MT4 cells as described in Example 1, Section 3. The region for recombination at the 5'-end of ΔProRT contains 188 nucleotides. The region for recombination at the 3'-end of ΔProRT is similar to the one described earlier (Kellam, P. and Larder, B. A. (1994) supra) and contains 130 nucleotides.

The length of these regions for recombination is not unimportant. Previous data (Bandyopadhyay, P. K. et al. Proc. Natl. Acad. Sci. U.S.A., (1984) 81, 3476–3480; Rubnitz, J. and Subramani, S. (1984) supra) demonstrate that a 10-fold reduction in recombination frequency may occur when sequence homology is reduced from 214 to 163 base pairs. Furthermore, sufficient recombination events should occur within the electroporated cells to ensure that the generated viral phenotype is a reliable reflection of the quasi-species present in the treated HIV-positive patient. Optimisation of recombinant events can first be achieved by adjusting the ratio of linearised proviral vector to RT-PCR fragment that is used for electroporation of the target cells. The standard method therefore,with typical results of outcome, has previously been described by Kellam, P. and Larder, B. A. (1994 supra ). As a consequence, it was decided to increase the initial input of about 2 μg of PCR product (with 10 μg of vector) to about 5 μg or more. The result thereof was reflected in a faster appearance of visible virus growth (cytopathogenic effect) in the culture of transfected cells.

Another option for optimisation of recombination events would be the design of primers resulting in longer recombination sequences.

Nevertheless, the real input in the transfection reaction always depends on the yield after PCR. Some samples have a high yield and as a result there will be a higher input of amplified material in the transfection reaction (with better results on efficiency of recombination).

However, despite a lower recombination efficiency, samples having a low yield can also be transfected and will result in viable virus with a reliable reflection of the virus population.

EXAMPLE 3

Alternative primers for RT-PCR of the ProRT sequence

New primers (A–D) have been designed relative to those used in Example 2 and should result in longer recombination sequences at both 5' and 3' end of the ProRT region. Two primers were designed at both the 5' and 3' end of the respective region to allow nested PCR. As indicated in FIGS. 3 and 4 the direct repeat present at the 5' end of the ProRT region was taken into account when designing the respective primers. The new primers are as follows:

```
A  PRTO-5  :5'-GCCCCTAGGA-AAAAGGGCTG-TTGG  (SEQ ID
                                            NO: 3)
B  PRTI-5  :5'-TGAAAGATTG-TACTGAGAGA-CAGG  (SEQ ID
                                            NO: 4)
C  PRTI-3  :5'-GATATTTCTC-ATGTTCATCT-TGGG  (SEQ ID
                                            NO: 5)
D  PRTO-3  :5'-AGGTGGCAGG-TTAAAATCAC-TAGC  (SEQ ID
                                            NO: 6)
```

EXAMPLE 4

Construction of an alternative ΔProRT vector:

As mentioned above, construction of an alternative ProRT deleted vector can be achieved by oligonucleotide-mediated mutagenesis. However, it is also possible to enlarge the ProRT deletion from the current 3'-end to the next KpnI site in the RT gene (40 base pairs further downstream). Ligation of a Klenow-treated KpnI site to a Klenow-treated BstEII site will restore the initial BstEII recognition sequence. As such, this alternative vector behaves similarly to the pGMT3-ΔPRT vector described in Example 2, but has a slightly larger RT deletion.

EXAMPLE 5

Figure 5:
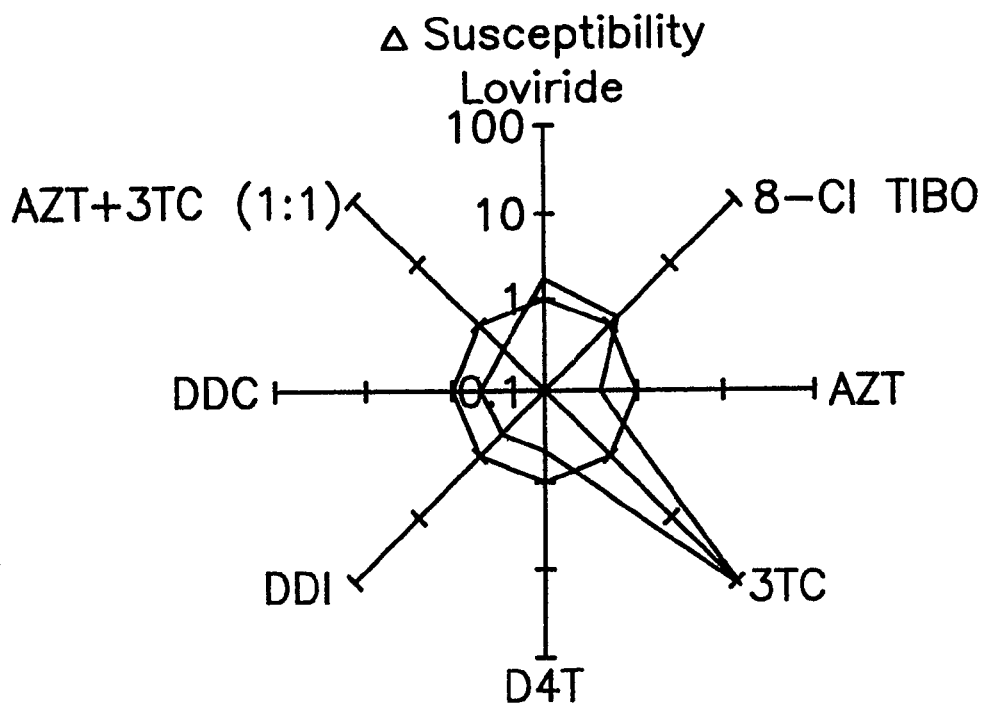
FIG. 5 is an Antivirogram for a patient harbouring 3TC resistant HIV strains as described in Example 5.

An HIV infected patient who received AZT from December 1989 until an undocumented later date, and switched to a combined chemotherapy of AZT+3TC (1:1) from February 1994 until October 1995 donated plasma whose susceptibility to a number of RT inhibitors was determined according to the above described protocol of Example 1. Recombinant wild type HIV strain recIIIB was used in said protocol as a reference HIV virus. Table 1 shows the $IC_{50}$ values ($\mu$M) measured and the ratio of said values. The Antivirogram is shown in FIG. 5.

TABLE 1

| | Anti-HIV-1 activity $IC_{50}$ ($\mu$M) | | | | |
|---|---|---|---|---|---|
| Drug | Exp. 1 | Exp. 2 | Mean (1) | recIIIB ref (2) | ratio (1)/(2) |
| loviride | 0.1 | 0.12 | 0.11 | 0.05 | 2 |
| tivirapine | 0.019 | 0.018 | 0.019 | 0.01 | 1.5 |
| AZT | 0.001 | 0.002 | 0.002 | 0.004 | 0.4 |
| 3TC | 31.6 | 100 | 65.8 | 0.56 | 118 |
| d4T | 0.07 | 0.49 | 0.06 | 0.12 | 0.5 |
| ddI | 2.0 | 0.8 | 1.4 | 2.83 | 0.5 |
| ddC | 0.2 | 0.2 | 0.2 | 0.38 | 0.5 |
| AZT + 3TC (1:1) | 0.001 | 0.001 | 0.001 | 0.002 | 0.5 |

From these data, one can determine that monotherapy with 3TC is unlikely to benefit this particular patient. Combined therapy of AZT+3TC (the current therapy), however, is still likely to exert a positive effect.

EXAMPLE 6

Figure 6:
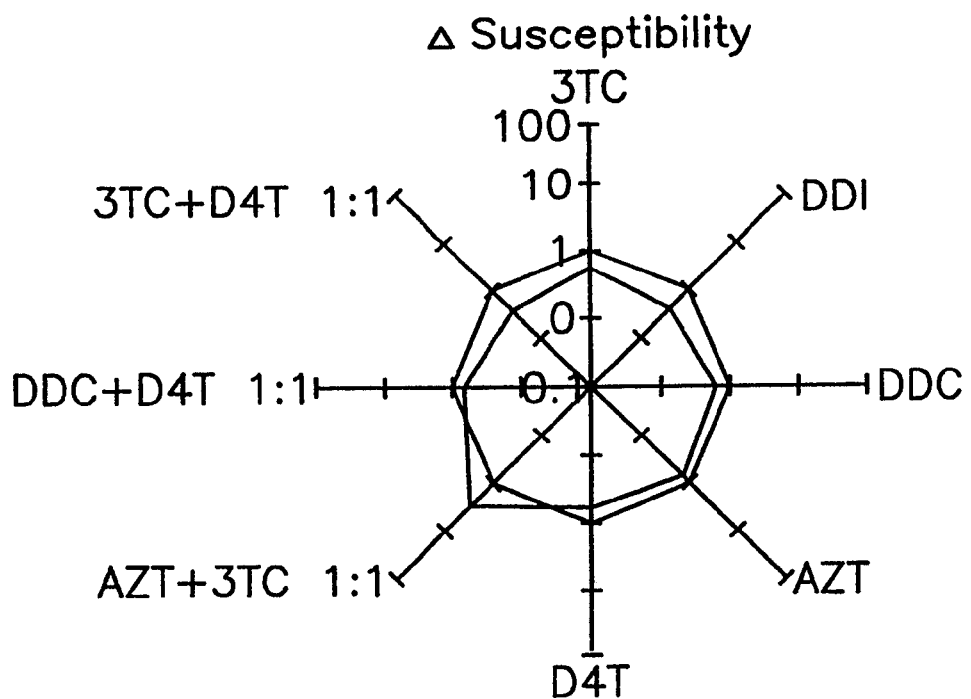
FIG. 6 is an Antivirogram for a drug-naive patient harbouring wild type like HIV strains as described in Example 6.

A drug-naive HIV infected patient donated plasma whose susceptibility to a number of RT inhibitors was determined according to the above described protocol of Example 1. Recombinant wild type HIV strain recIIIB was used in said protocol as a reference HIV virus. Table 2 shows the $IC_{50}$ values ($\mu$M) measured and the ratio of said values. An Antivirogram was prepared and shown in FIG. 6.

TABLE 2

| | Anti-HIV-1 activity $IC_{50}$ ($\mu$M) | | | | |
|---|---|---|---|---|---|
| Drug | Exp. 1 | Exp. 2 | Mean (1) | recIIIB ref (2) | ratio (1)/(2) |
| 3TC | 1.81 | 2.02 | 1.91 | 3.08 | 1 |
| ddI | 3.07 | 4.47 | 3.77 | 8.58 | 0.4 |
| ddC | 1.45 | 1.47 | 1.46 | 2.21 | 1 |
| AZT | 0.04 | 0.05 | 0.05 | 0.06 | 1 |
| d4T | 1.31 | 0.97 | 1.14 | 1.74 | 1 |
| AZT + 3TC (1:1) | 0.05 | 0.04 | 0.05 | 0.02 | 3 |
| DDC + D4T (1:1) | 0.62 | 0.44 | 0.53 | 0.77 | 1 |
| 3TC + d4T (1:1) | 0.42 | 0.44 | 0.43 | 1.11 | 0.4 |

From these data one can determine that the patient is infected with HIV strains closely resembling the wild type HIV. None of the drug regimens is to be excluded, so chemotherapy can be initiated with a drug such as AZT having a positive track record.

EXAMPLE 7

Figure 7A:
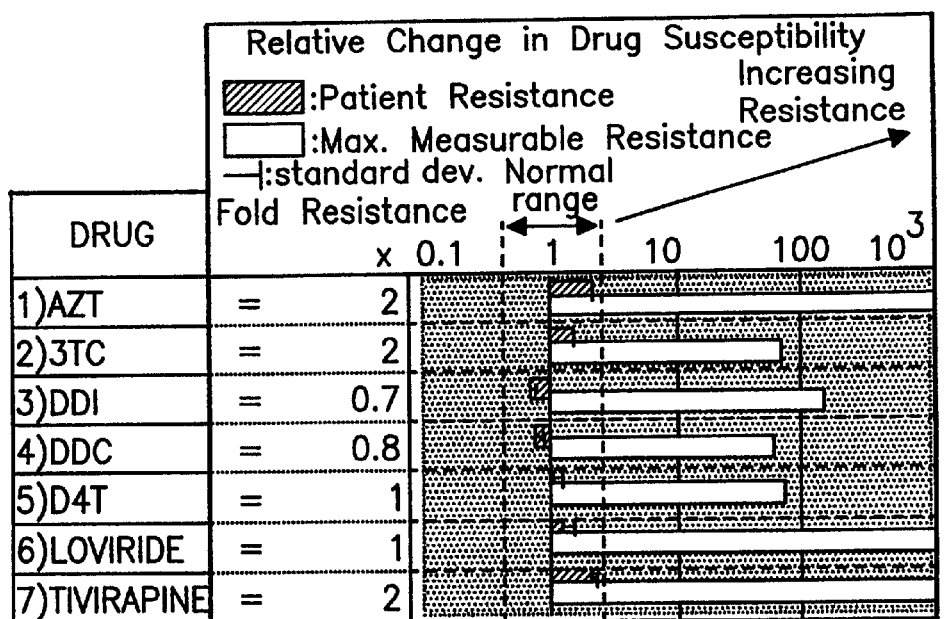
FIG. 7A is a bar graph showing relative change in drug susceptibility for the patient of Example 7.
Figure 7B:
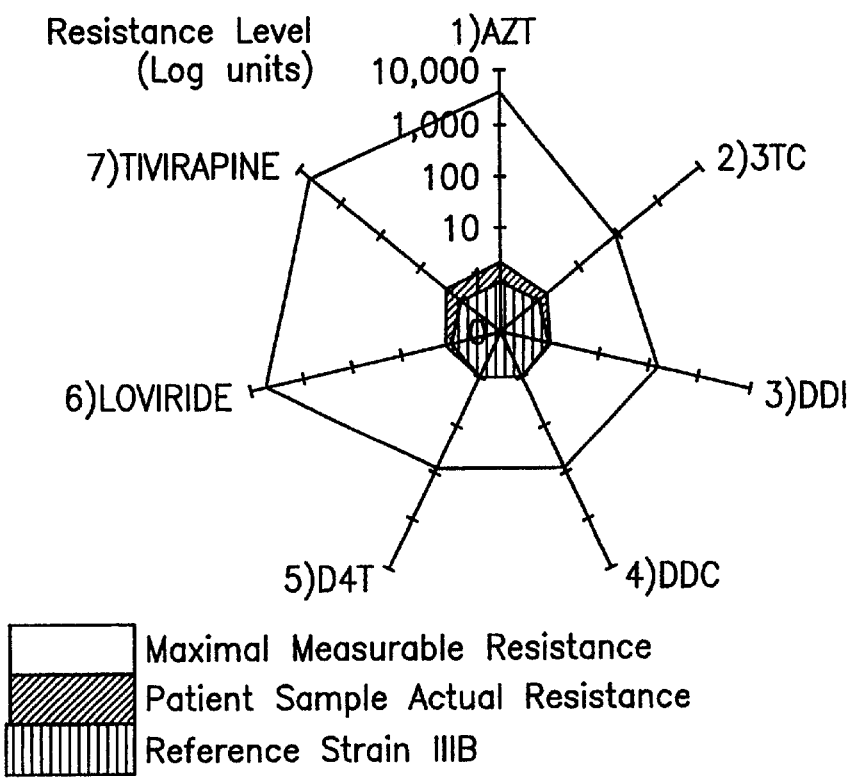
FIG. 7B is an Antivirogram for the patient the subject of Example 7.

A drug-naive HIV-infected patient donated plasma whose susceptibility to a number of RT inhibitors was determined according to the protocol set out in Example 1. Recombinant wild type HIV strain recIIIB was used as a reference HIV virus. Table 3 shows the $IC_{50}$ values ($\mu$M) measured and the ratio of said values. A bar graph showing relative change in drug susceptibility is shown in FIG. 7A. An Antivirogram was also prepared and is shown in FIG. 7B.

TABLE 3

| | Anti-HIV-1 activity $IC_{50}$ ($\mu$M) | | | | |
|---|---|---|---|---|---|
| Drug | Exp. 1 | Exp. 2 | Mean (1) | recIIIB ref (2) | ratio (1)/(2) |
| AZT | 0.052 | 0.050 | 0.051 | 0.023 | 2 |
| 3TC | 2.173 | ND | 2.173 | 1.381 | 2 |
| ddI | 0.475 | 0.429 | 0.452 | 0.648 | 0.7 |
| ddC | 1.042 | 1.389 | 1.216 | 1.616 | 0.8 |
| d4T | 1.142 | 1.657 | 1.399 | 1.368 | 1 |
| loviride | 0.035 | 0.025 | 0.030 | 0.024 | 1 |
| tivirapine | 0.042 | 0.049 | 0.046 | 0.021 | 2 |

From these data one can determine that the patient is infected with a HIV strain closely resembling the wild type HIV. None of the drug regimens is to be excluded, so chemotherapy can be initiated with a drug such as AZT, 3TC or others having a positive track record.

EXAMPLE 8

Figure 8A:
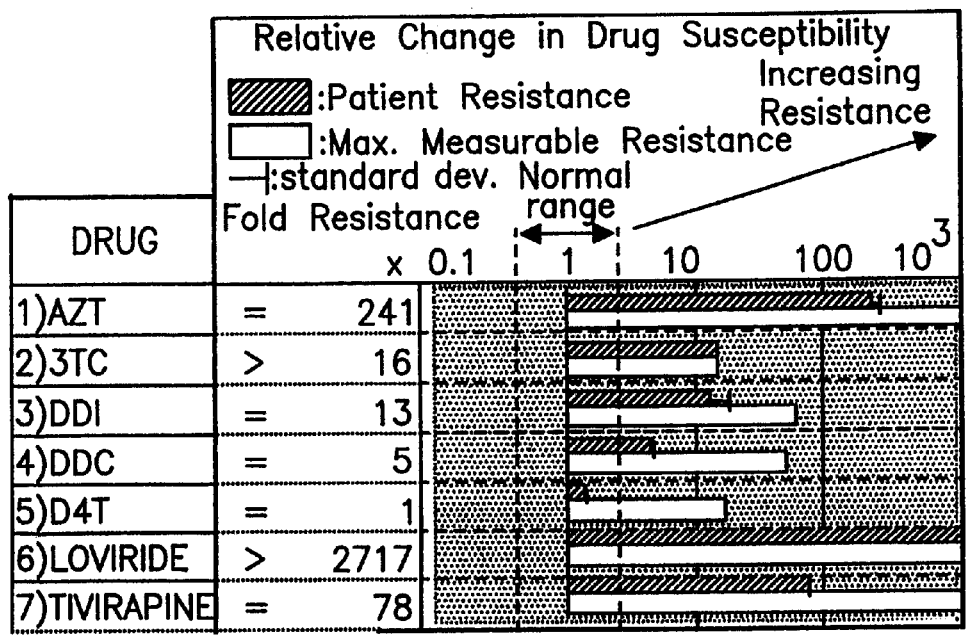
FIG. 8A is a bar graph showing relative change in drug susceptibility for the patient of Example 8.
Figure 8B:
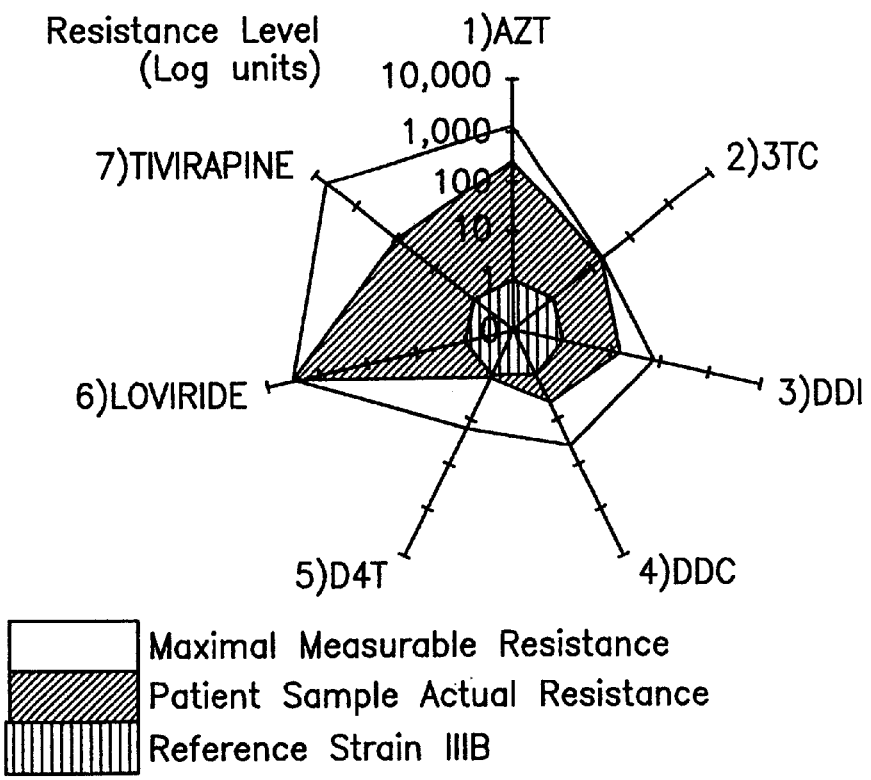
FIG. 8B is an Antivirogram for the patient the subject of Example 8.

An HIV-infected patient with a therapy history including AZT, 3TC and loviride donated plasma whose susceptibility to a number of RT inhibitors was determined according to the protocol set out in Example 1. Recombinant wild type HIV strain recIIIB was used as a reference HIV virus. Table 4 shows the $IC_{50}$ values ($\mu$M) measured and the ratio of said values. A bar graph showing relative change in drug susceptability is shown in FIG. 8A. An Antivirogram was also prepared and is shown in FIG. 8B.

TABLE 4

Anti-HIV-1 activity
IC$_{50}$ ($\mu$M)

| Drug | Exp. 1 | Exp. 2 | Mean (1) | recIIIB ref (2) | ratio (1)/(2) |
|---|---|---|---|---|---|
| AZT | 18.264 | 22.251 | 20.257 | 0.084 | 241 |
| 3TC | >100.000 | >100.000 | >100.000 | 6.304 | >16 |
| ddI | 26.861 | 15.435 | 21.148 | 1.586 | 13 |
| ddC | 9.290 | 8.506 | 8.898 | 1.931 | 5 |
| d4T | 7.500 | 7.097 | 7.298 | 5.465 | 1 |
| loviride | >100.000 | >100.000 | >100.000 | 0.037 | >2717 |
| tivirapine | 1.626 | 1.604 | 1.615 | 0.021 | 78 |

From this data one can determine that the patient is infected with a HIV strain displaying a decreased susceptibility towards most of the nucleoside and non-nucleoside antiretroviral drugs examined. Therapy can still be initiated with D4T or DDC. The possibility of including protease-inhibitors into the therapy can be considered.

EXAMPLE 9

Figure 9A:
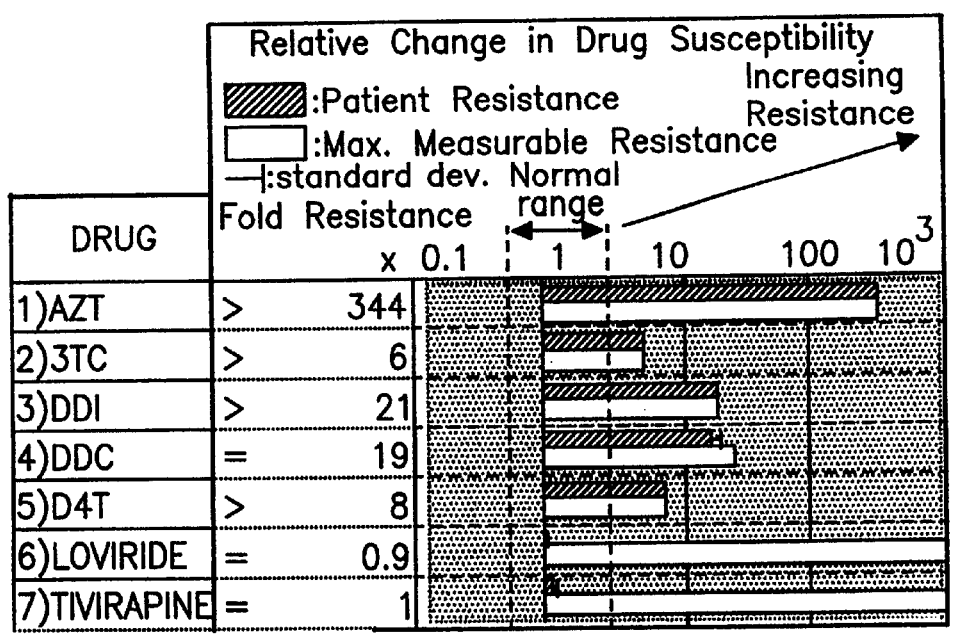
FIG. 9A is a bar graph showing relative change in drug susceptibility for the patient of Example 9.
Figure 9B:
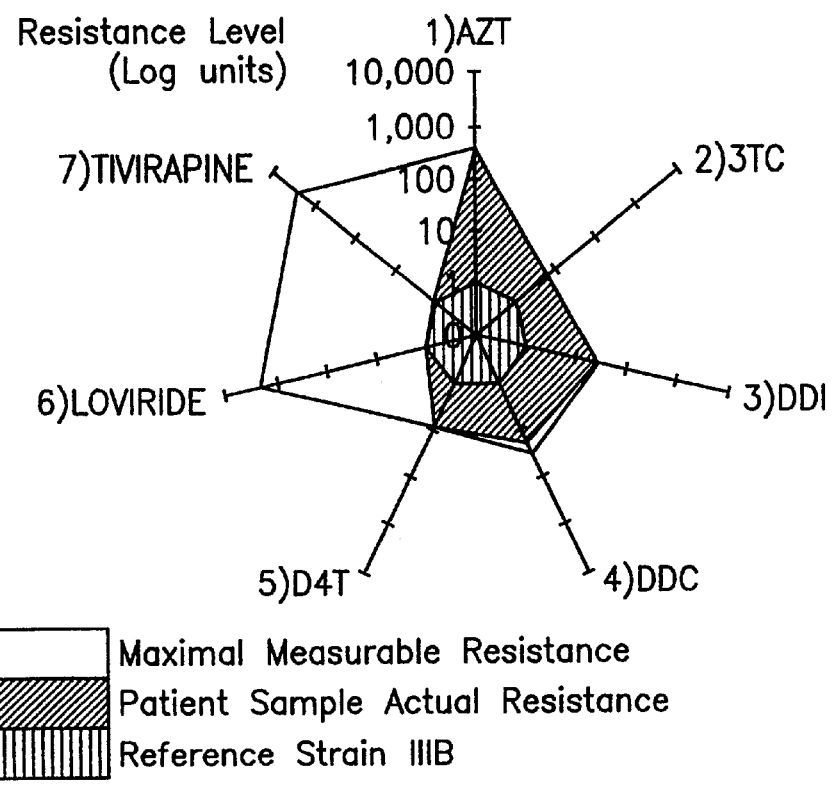
FIG. 9B is an Antivirogram for the patient the subject of Example 9.

An HIV-infected patient with a therapy history including multiple nucleoside analogue RT-inhibitors donated plasma whose susceptibility to a number of RT inhibitors was determined according to the protocol set out in Example 1. Recombinant wild type HIV strain recIIIB was used as a reference HIV virus. Table 5 shows the IC$_{50}$ values ($\mu$M) measured and the ratio of said values. A bar graph showing relative change in drug susceptibility is shown in FIG. 9A. An Antivirogram was also prepared and is shown in FIG. 9B.

TABLE 5

Anti-HIV-1 activity
IC$_{50}$ ($\mu$M)

| Drug | Exp. 1 | Exp. 2 | Mean (1) | recIIIB ref (2) | ratio (1)/(2) |
|---|---|---|---|---|---|
| AZT | >100.000 | ND | >100.000 | 0.291 | >344 |
| 3TC | >100.000 | >100.000 | >100.000 | 16.670 | >6 |
| ddI | >100.000 | >100.000 | >100.000 | 4.757 | >21 |
| ddC | 60.079 | 73.049 | 66.564 | 3.444 | 19 |
| d4T | >100.000 | >100.000 | >100.000 | 12.030 | >8 |
| loviride | 0.064 | 0.058 | 0.061 | 0.065 | 0.9 |
| tivirapine | 0.052 | 0.043 | 0.048 | 0.042 | 1 |

From this data one can determine that the patient is infected with a HIV strain displaying a decreased susceptibility towards all nucleoside analogue antiretroviral drugs. Non-nucleoside antiretroviral drugs should not be excluded from therapy. Here also, the possibility of including protease inhibitors into the therapy can be considered.

EXAMPLE 10

Figure 10A:
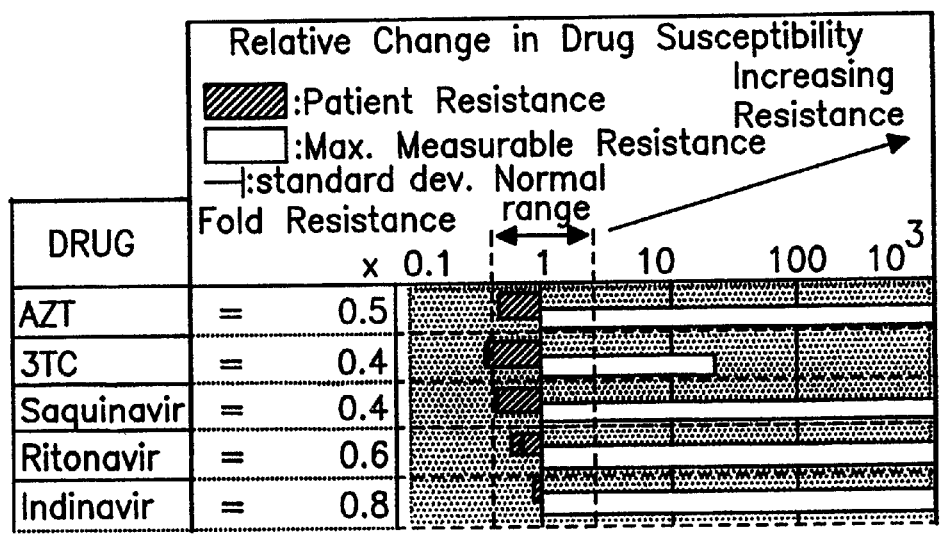
FIG. 10A is a bar graph showing relative change in drug susceptibility for the patient of Example 10.
Figure 10B:
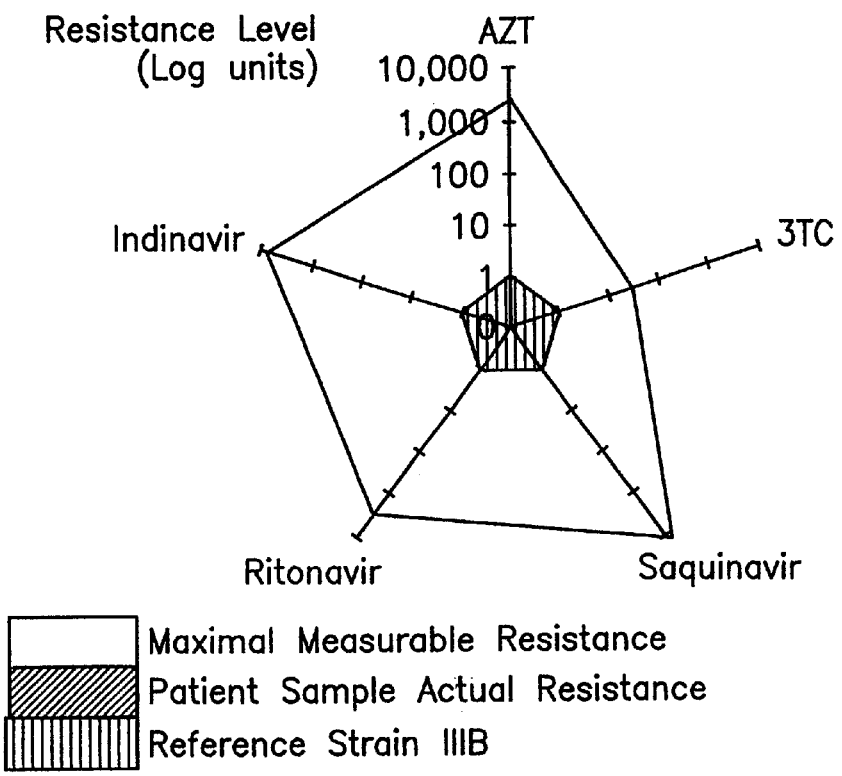
FIG. 10B is an Antivirogram for the patient the subject of Example 10.

A drug-naive HIV-infected patient donated plasma whose susceptibility to a number of RT inhibitors and protease inhibitors was determined according to the protocol set out in Example 1. Recombinant wild type HIV strain recIIIB was used as a reference HIV virus. Table 6 shows the IC$_{50}$ values ($\mu$M) measured and the ratio of said values. A bar graph showing relative change in drug susceptibility is shown in FIG. 10A. An Antivirogram was also prepared and is shown in FIG. 10B.

TABLE 6

Anti-HIV-1 activity
IC$_{50}$ ($\mu$M)

| Drug | Exp. 1 | Exp. 2 | Mean (1) | recIIIB ref (2) | ratio (1)/(2) |
|---|---|---|---|---|---|
| AZT | 0.019 | 0.019 | 0.019 | 0.041 | 0.5 |
| 3TC | 1.525 | 1.718 | 1.622 | 4.608 | 0.4 |
| saquinavir | 0.003 | 0.003 | 0.003 | 0.006 | 0.4 |
| ritonavir | 0.022 | 0.017 | 0.019 | 0.033 | 0.6 |
| indinavir | 0.013 | 0.013 | 0.013 | 0.016 | 0.8 |

From these data one can determine that the patient is infected with HIV strains closely resembling the wild type HIV. None of the drug regimens is to be excluded, so that chemotherapy can be initiated with a drug such as AZT, 3TC or others having a positive track record.

EXAMPLE 11

Figure 11A:
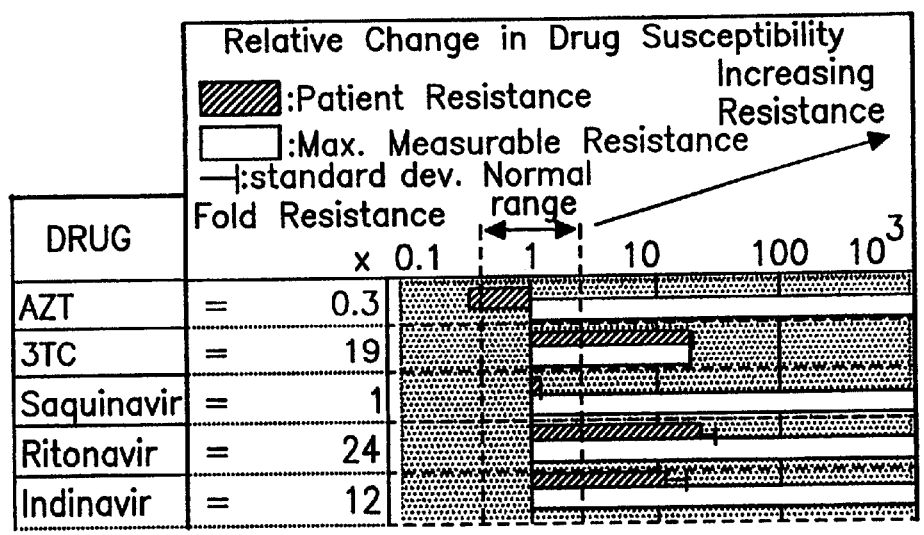
FIG. 11A is a bar graph showing relative change in drug susceptibility for the patient of Example 11.
Figure 11B:
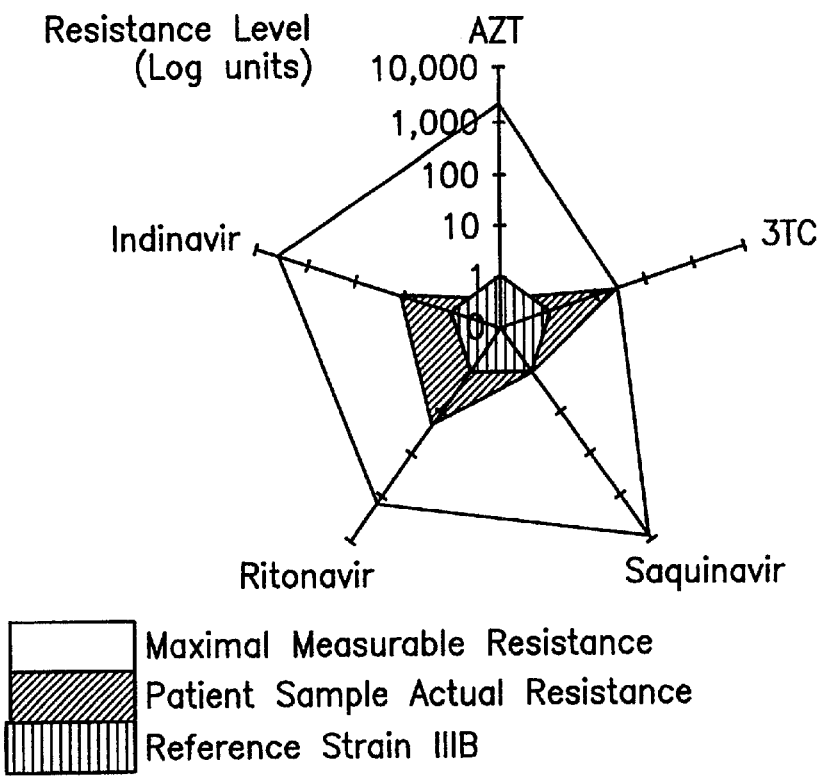
FIG. 11B is an Antivirogram for the patient the subject of Example 11.

An HIV infected patient with a therapy history including RT and protease inhibitors donated plasma whose susceptibility to a number of RT inhibitors and protease inhibitors was determined according to the protocol set out in Example 1. Recombinant wild type HIV strain recIIIb was used as a reference HIV virus. Table 7 shows the IC$_{50}$ values ($\mu$M) measured and the ratio of said values. A bar graph showing relative change in drug susceptibility is shown in FIG. 11A. An Antivirogram was also prepared and is shown in FIG. 11B.

TABLE 7

Anti-HIV-1 activity
IC$_{50}$ ($\mu$M)

| Drug | Exp. 1 | Exp. 2 | Mean (1) | recIIIB ref (2) | ratio (1)/(2) |
|---|---|---|---|---|---|
| AZT | ND | 0.015 | 0.015 | 0.047 | 0.3 |
| 3TC | >100.000 | 93.962 | 96.981 | 5.178 | 19 |
| saquinavir | 0.014 | 0.015 | 0.014 | 0.012 | 1 |
| ritonavir | 1.198 | 1.739 | 1.468 | 0.062 | 24 |
| indinavir | 0.229 | 0.416 | 0.323 | 0.027 | 12 |

From these data one can determine that the patient is infected with a HIV strain displaying a decreased susceptibilty towards the RT-inhibitor 3TC and protease inhibitors indinavir and ritonavir. Accordingly, chemotherapy can be adjusted with drugs such as AZT or saquinavir having a positive track record.

EXAMPLE 12

Figure 12A:
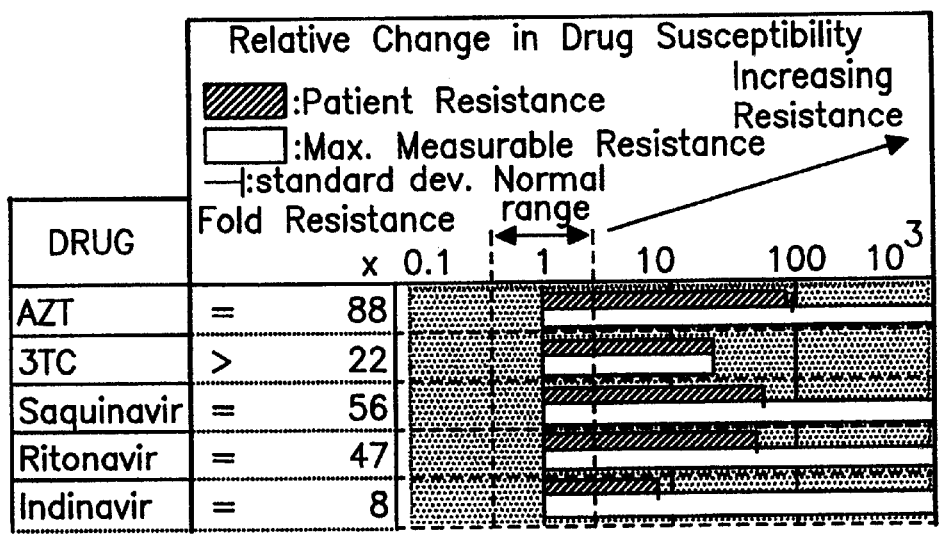
FIG. 12A is a bar graph showing relative change in drug susceptibility for the patient of Example 12.
Figure 12B:
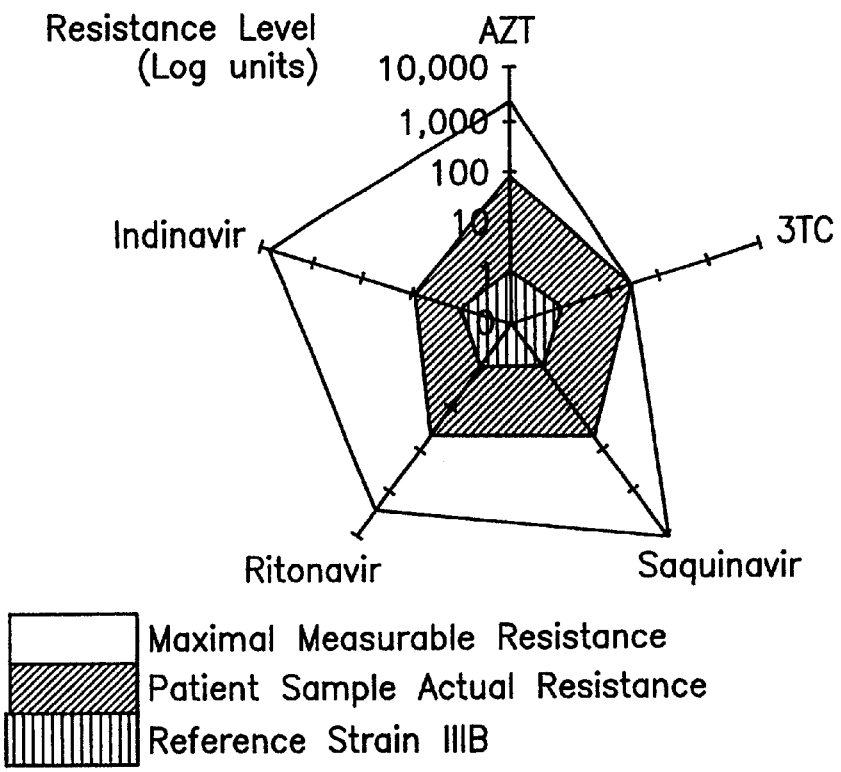
FIG. 12B is an Antivirogram for the patient the subject of Example 12.

An HIV infected patient with a therapy history including RT and protease inhibitors donated plasma whose susceptibility to a number of RT inhibitors and protease inhibitors was determined according to the protocol set out in Example 1. Table 8 shows the IC$_{50}$ values ($\mu$M) measured and the ratio of said values. A bar graph showing relative change in drug susceptibility is shown in FIG. 12A. An Antivirogram was also prepared and is shown in FIG. 12B.

TABLE 8

| Drug | Anti-HIV-1 activity IC$_{50}$ ($\mu$M) | | | | ratio (1)/(2) |
|---|---|---|---|---|---|
| | Exp. 1 | Exp. 2 | Mean (1) | recIIIB ref (2) | |
| AZT | 3.833 | 3.355 | 3.594 | 0.041 | 88 |
| 3TC | >100.000 | >100.000 | >100.000 | 4.608 | 22 |
| saquinavir | 0.350 | 0.352 | 0.351 | 0.006 | 56 |
| ritonavir | 1.610 | 1.530 | 1.570 | 0.033 | 47 |
| indinavir | 0.124 | ND | 0.124 | 0.016 | 8 |

From these data one can determine that the patient is infected with a HIV strain displaying a decreased susceptibility towards RT-inhibitors 3TC and AZT and protease inhibitors indinavir, ritonavir and saquinavir.

EXAMPLE 13

Comparison of Phenotyping relative to Genotyping

Plasma samples were obtained from HIV-infected individuals who had been receiving non-nucleoside RT inhibitor (NNRTI) long-term monotherapy. HIV-RNA was extracted, reverse-transcribed and amplified as described in Example 1. Starting from outer PCR material of positive samples, the first 785 nucleotides of the RT gene were amplified and this material was further used for genotyping.

Briefly, the 785 nucleotide fragment was subjected to cycle-sequencing reactions using the ThermoSequenase (ThermoSequenase is a Trade Mark) fluorescent labelled primer cycle sequencing kit with 7-deaza-dGTP from Amersham (cat# RPN2438). Four sequencing primers, chosen to allow for sequence determination in both directions from nucleotide 27 to nucleotide 681 of the RT gene, were used for each sample. The reactions were analysed on an ALF (ALF is a Trade Mark) automatic sequencer (Pharmacia). The generated sequences were exported to a Power Macintosh and further analysed with the GeneWorks 2.5 software (Oxford Molecular Group Inc.). Resulting amino acid sequences were compared with the corresponding sequence of the laboratory HIV-1 clone HXB2D and resistance-associated mutations identified in patient material. The results are shown in Table 9 where the one-letter amino acid code is used.

TABLE 9

| | RESISTANCE ASSOCIATED MUTATIONS | | | | | | | | | | | | | FOLD RESISTANCE TO | | | |
|---|---|---|---|---|---|---|---|---|---|---|---|---|---|---|---|---|---|
| P | M 41 | D 67 | K 70 | A 98 | K 101 | K 103 | V 108 | E 138 | Y 181 | M 184 | G 190 | T 215 | K 219 | AZT | 3TC | NNRTI 1 | NNRTI 2 |
| 1 | | | | | | N | | | | | | | | 1 | 1 | 56 | 437 |
| 2 | | | | | | S | | | | | | | | 1 | 0.4 | 102 | 53 |
| 3 | | | | | | N | | | | | | | | 0.4 | 1 | 36 | 87 |
| 4 | | | | | | | | | | | | | | 0.3 | 0.1 | 1 | 0.4 |
| 5 | | | | | | | | | | | | | | 1 | 0.4 | 4 | 3 |
| 6 | | | | | | N | | | | | | | | 1 | 0.3 | 103 | 245 |
| 7 | | | | | | S | | | | | | | | 1 | 0.04 | 112 | 57 |
| 8 | | | | | | N | | | | | | | | 1 | 1 | 30 | 81 |
| 9 | | | | | | | | | C | | | | | 2 | 1 | >1432 | 12 |
| 10 | | | | | | N | | | | | | | | 0.4 | 0.1 | 53 | 172 |
| 11 | L | N | R | | | N | | | V | | F | | Q | 94 | >8 | 321 | 669 |
| 12 | L | | | | | | | | | | | Y | | 28 | 2 | 1 | 3 |
| 13 | | | | | E | K/N | | A | | | G/A | Not Det | | 1 | 1 | >1466 | 455 |
| 14 | | | | | | N | | | | | | | | 1 | 1 | 93 | 349 |
| 15 | | | | | | N | | | | | | | | 2 | 1 | >2424 | 449 |
| 16 | | | | | | N | | | V | | | | | 1 | >8 | 21 | 115 |
| 17 | | | | | | N | | | | | | | | 1 | 1 | 29 | 102 |
| 18 | | | | | | S | | | | | | | | 1 | 1 | 95 | 181 |
| 19 | | | | | | N | | | | | | | | 1 | 1 | 78 | 260 |
| 20 | | | | G | | | | | | | | | | 0.4 | 1 | 22 | 25 |
| 21 | | | | | | N | | | | | | | | 1 | 0.4 | 47 | 68 |
| 22 | | | | | | | I | | | | | | | 1 | 0.4 | 3 | 3 |
| 23 | | | | | | N | | | | | | | | 0.2 | 0.2 | 9 | 9 |
| 24 | | | | | | Q | | | | | | | | 1 | 1 | 7 | 59 |

P = Patient

The top row of Table 9 shows the aminoacids (AA) found in the wild type sequence and their position. Amino acids changes at these positions are shown for each patient in the following rows. Only the positions at which changes were observed in patient material are shown. The right part of Table 9 presents the fold resistance to different RT inhibitors as determined by the method according to the invention for each of the patients' samples. NNRTI 1 is the non-nucleoside RT inhibitor that was administered to the patients. NNRTI 2 is another non-nucleoside RT inhibitor for which cross-resistance with the first one was observed to some extent.

The genotyping results regarding nucleoside analog RT inhbitors resistance are as follows:

M41L, D67N, K70R, T215F/Y and K219Q/E are AZT resistance-associated mutations (Larder, B. and Kemp, S. (1989) Science 246, 1155–1158; Kellam, P. et al. (1992) PNAS 89, 1934–1938). Their presence, individually or in different combinations, in the genome of HIV isolated from patient material correlates with the phenotypic resistance as determined by the Antivirogram generated (patients 11 and 12).

The same applies to resistance to 3TC associated with the MI 84V mutation (Tisdale, M. et al. (1993) PNAS 90, 5653–5656) which is observed only in the patients which show phenotypic resistance to the drug (patients 11 and 16).

The genotyping results regarding NNRTIs resistance are as follows:

Three patients (3, 4 and 12) have no NNRTI resistance-associated mutation and are phenotypically sensitive to the drug.

Most of the patients who show phenotypic resistance to the NNRTIs have a NNRTI resistance-associated mutation at position 103 (K103N/S).

One patient (9) has the Y181 C. NNRTI resistance-associated mutation and shows a high phenotypic resistance (>1432 fold) to NNRTI 1.

Patient 13 has several NNRTI resistance-associated mutations (K101E, K103N partially and G190A partially). This patient also shows a high phenotypic resistance (>1466 fold) to NNRTI 1. The E138A mutation observed in this sample is not associated so far with resistance. However, another mutation at this same position, i.e. E138K, has been demonstrated to play an important role in resistance to the TSAO compounds (Balzarini, J. et al. (1993) PNAS 90, 6952–9656). The role of the E138A mutation still needs to be assessed.

Patient 20 has the A98G NNRTI resistance-associated mutation and shows phenotypic resistance to the tested NNRTIs.

Patient 22 has the V108I NNRTI resistance-associated mutation but does not show any phenotypic resistance to the tested NNRTIs.

Patient 24 shows no NNRTI resistance-associated mutation (the K101Q mutation is found in several HIV-1 wild type genomes) but is phenotypically resistant to the tested NNRTIs.

What is claimed is:

1. A plasmid designated pGEMT3-ΔPRT and deposited at the Belgian Coordinated Collections of Microorganisms-BCCM LMBP-Collection on Nov. 8, 1996, under the deposit number LMBP3590.

2. The plasmid of claim 1, further comprising an HIV pol gene isolated from an HIV-infected host.

3. A cell comprising the plasmid of claim 1.

4. An assay for managing HIV chemotherapy of patients who are HIV positive, comprising a plasmid designated pGEMT3 -ΔPRT and deposited at the Belgian Coordinated Collections of Microorganisms-BCCM LMBP-Collection on Nov. 8, 1996, under the deposit number LMBP3590.

5. The assay of claim 4, further comprising a chimeric strain of HIV.

6. The assay of claim 4 further comprising a cell line susceptible to HIV infection.

7. The assay of claim 6, wherein the cell line is a CD4+ cell T-cell line.

8. The assay of claim 7, wherein the CD4+ T-cell line is MT4.

9. The assay of claim 6, wherein the cell line is a HeLa cell line.

10. The assay of claim 4, further comprising one or more inhibitors of an expressed product of the pol gene of HIV.

11. The assay of claim 10, wherein the expressed product of the pol gene of HIV is selected from the group consisting of HIV reverse transcriptase (RT), protease and integrase.

12. The assay of claim 4, further comprising a biological sample.

* * * * *

SEQUENCE LISTING

<160> NUMBER OF SEQ ID NOS: 15

<210> SEQ ID NO 1
<211> LENGTH: 33
<212> TYPE: DNA
<213> ORGANISM: Human immunodeficiency virus type 1

<400> SEQUENCE: 1
cattgctctc caattactgt gatatttctc atg         33

<210> SEQ ID NO 2
<211> LENGTH: 26
<212> TYPE: DNA
<213> ORGANISM: Human immunodeficiency virus type 1

<400> SEQUENCE: 2
gggaagatct ggccttccta caaggg         26

<210> SEQ ID NO 3
<211> LENGTH: 24
<212> TYPE: DNA
<213> ORGANISM: Human immunodeficiency virus type 1

<400> SEQUENCE: 3
gcccctagga aaagggctg ttgg         24

<210> SEQ ID NO 4
<211> LENGTH: 24
<212> TYPE: DNA
<213> ORGANISM: Human immunodeficiency virus type 1

-continued

```
<400> SEQUENCE: 4
tgaaagattg tactgagaga cagg                                            24

<210> SEQ ID NO 5
<211> LENGTH: 24
<212> TYPE: DNA
<213> ORGANISM: Human immunodeficiency virus type 1

<400> SEQUENCE: 5
gatatttctc atgttcatct tggg                                            24

<210> SEQ ID NO 6
<211> LENGTH: 24
<212> TYPE: DNA
<213> ORGANISM: Human immunodeficiency virus type 1

<400> SEQUENCE: 6
aggtggcagg ttaaaatcac tagc                                            24

<210> SEQ ID NO 7
<211> LENGTH: 2601
<212> TYPE: DNA
<213> ORGANISM: HIV-HXB2
<220> FEATURE:
<221> NAME/KEY: CDS
<222> LOCATION: (1)..(492)
<223> OTHER INFORMATION: gag Polyprotein

<400> SEQUENCE: 7 gga cca gcg gct aca cta gaa gaa atg atg aca gca tgt cag gga gta       48
Gly Pro Ala Ala Thr Leu Glu Glu Met Met Thr Ala Cys Gln Gly Val
 1               5                  10                  15 gga gga ccc ggc cat aag gca aga gtt ttg gct gaa gca atg agc caa       96
Gly Gly Pro Gly His Lys Ala Arg Val Leu Ala Glu Ala Met Ser Gln
             20                  25                  30 gta aca aat tca gct acc ata atg atg cag aga ggc aat ttt agg aac      144
Val Thr Asn Ser Ala Thr Ile Met Met Gln Arg Gly Asn Phe Arg Asn
         35                  40                  45 caa aga aag att gtt aag tgt ttc aat tgt ggc aaa gaa ggg cac aca      192
Gln Arg Lys Ile Val Lys Cys Phe Asn Cys Gly Lys Glu Gly His Thr
     50                  55                  60 gcc aga aat tgc agg gcc cct agg aaa aag ggc tgt tgg aaa tgt gga      240
Ala Arg Asn Cys Arg Ala Pro Arg Lys Lys Gly Cys Trp Lys Cys Gly
 65                  70                  75                  80 aag gaa gga cac caa atg aaa gat tgt act gag aga cag gct aat ttt      288
Lys Glu Gly His Gln Met Lys Asp Cys Thr Glu Arg Gln Ala Asn Phe
                 85                  90                  95 tta ggg aag atc tgg cct tcc tac aag gga agg cca ggg aat ttt ctt      336
Leu Gly Lys Ile Trp Pro Ser Tyr Lys Gly Arg Pro Gly Asn Phe Leu
            100                 105                 110 cag agc aga cca gag cca aca gcc cca cca gaa gag agc ttc agg tct      384
Gln Ser Arg Pro Glu Pro Thr Ala Pro Pro Glu Glu Ser Phe Arg Ser
        115                 120                 125 ggg gta gag aca aca act ccc cct cag aag cag gag ccg ata gac aag      432
Gly Val Glu Thr Thr Thr Pro Pro Gln Lys Gln Glu Pro Ile Asp Lys
    130                 135                 140 gaa ctg tat cct tta act tcc ctc agg tca ctc ttt ggc aac gac ccc      480
Glu Leu Tyr Pro Leu Thr Ser Leu Arg Ser Leu Phe Gly Asn Asp Pro
145                 150                 155                 160 tcg tca caa taa agatagggggg caactaaag gaagctctat tagatacagg           532
Ser Ser Gln
```

```
agcagatgat acagtattag aagaaatgag tttgccagga agatggaaac caaaaatgat      592 aggggaatt ggaggtttta tcaaagtaag acagtatgat cagatactca tagaaatctg       652
tggacataaa gctataggta cagtattagt aggacctaca cctgtcaaca taattggaag      712
aaatctgttg actcagattg gttgcacttt aaattttccc attagcccta ttgagactgt      772
accagtaaaa ttaaagccag gaatggatgg cccaaaagtt aaacaatggc cattgacaga      832
agaaaaaata aaagcattag tagaaatttg tacagatatg gaaaaggaag cgaaaatttc      892
aaaaattggg cctgaaaatc catacaatac tccagtattt gccataaaga aaaagacag      952 tactaaatgg agaaaattag tagatttcag agaacttaat aagagaactc aagacttctg      1012
ggaagttcaa ttaggaatac cacatcccgc aggcttaaaa aagaaaaaat cagtaacagt      1072
actggatgtg ggtgatgcat attttcagt tcccttagat aaagactca ggaagtatac        1132 tgcatttacc atacctagta taaacaatga gacaccaggg attagatatc agtacaatgt      1192
gcttccacag ggatggaaag gatcaccagc aatattccaa agtagcatga caaaaatctt      1252
agagcctttt agaaaacaaa atccagacat agttatctat caatacatgg atgatttgta      1312
tgtaggatct gacttagaaa tagggcagca tagaacaaaa atagaggagc tgagacaaca      1372
tctgttgagg tggggactta ccacaccaga caaaaaacat cagaaagaac ctccattcct      1432
ttggatgggt tatgaactcc atcctgataa atggacagta cagcctatag tgctgccaga      1492
aaaagacagc tggactgtca atgacataca gaagttagtg gggaaattga attgggcaag      1552
tcagatttac ccagggatta aagtaaggca attatgtaaa ctccttagag gaaccaaagc      1612
actaacagaa gtaataccac taacagaaga agcagagcta gaactggcag aaaacagaga      1672
gattctaaaa gaaccagtac atggagtgta ttatgaccca tcaaaagact aatagcaga      1732 aatacagaag caggggcaag gccaatggac atatcaaatt tatcaagagc catttaaaaa      1792
tctgaaaaca ggaaaatatg caagaatgag gggtgcccac actaatgatg taaaacaatt      1852
aacagaggca gtgcaaaaaa taaccacaga aagcatagta atatgggga agactcctaa      1912 atttaaactg cccatacaaa aggaaacatg gaaacatgg tggacagagt attggcaagc      1972
cacctggatt cctgagtggg agtttgttaa taccctccc ttagtgaaat tatggtacca       2032
gttagagaaa gaacccatag taggagcaga aaccttctat gtagatgggg cagctaacag      2092
ggagactaaa ttaggaaaag caggatatgt tactaataga ggaagacaaa aagttgtcac      2152
cctaactgac acaacaaatc agaagactga gttacaagca atttatctag ctttgcagga      2212
ttcgggatta gaagtaaaca tagtaacaga ctcacaatat gcattaggaa tcattcaagc      2272
acaaccagat caaagtgaat cagagttagt caatcaaata atagagcagt taataaaaaa      2332
ggaaaaggtc tatctggcat gggtaccagc acacaaagga attggaggaa atgaacaagt      2392
agataaatta gtcagtgctg gaatcaggaa agtactattt ttagatggaa tagataaggc      2452
ccaagatgaa catgagaaat atcacagtaa ttggagagca atggctagtg atttaacct      2512 gccacctgta gtagcaaaag aaatagtagc cagctgtgat aaatgtcagc taaaaggaga      2572
agccatgcat ggacaagtag actgtagtc                                         2601
```

<210> SEQ ID NO 8
<211> LENGTH: 163
<212> TYPE: PRT
<213> ORGANISM: HIV-HXB2

<400> SEQUENCE: 8

```
Gly Pro Ala Ala Thr Leu Glu Glu Met Met Thr Ala Cys Gln Gly Val
 1               5                  10                  15

Gly Gly Pro Gly His Lys Ala Arg Val Leu Ala Glu Ala Met Ser Gln
                20                  25                  30

Val Thr Asn Ser Ala Thr Ile Met Met Gln Arg Gly Asn Phe Arg Asn
            35                  40                  45

Gln Arg Lys Ile Val Lys Cys Phe Asn Cys Gly Lys Glu Gly His Thr
    50                  55                  60

Ala Arg Asn Cys Arg Ala Pro Arg Lys Lys Gly Cys Trp Lys Cys Gly
65                  70                  75                  80

Lys Glu Gly His Gln Met Lys Asp Cys Thr Glu Arg Gln Ala Asn Phe
                85                  90                  95

Leu Gly Lys Ile Trp Pro Ser Tyr Lys Gly Arg Pro Gly Asn Phe Leu
            100                 105                 110

Gln Ser Arg Pro Glu Pro Thr Ala Pro Pro Glu Glu Ser Phe Arg Ser
        115                 120                 125

Gly Val Glu Thr Thr Thr Pro Pro Gln Lys Gln Glu Pro Ile Asp Lys
    130                 135                 140

Glu Leu Tyr Pro Leu Thr Ser Leu Arg Ser Leu Phe Gly Asn Asp Pro
145                 150                 155                 160

Ser Ser Gln

<210> SEQ ID NO 9
<211> LENGTH: 2601
<212> TYPE: DNA
<213> ORGANISM: HIV-HXB2
<220> FEATURE:
<221> NAME/KEY: CDS
<222> LOCATION: (334)..(489)
<223> OTHER INFORMATION: gag P6 (52 AA)

<400> SEQUENCE: 9
ggaccagcgg ctacactaga agaaatgatg acagcatgtc agggagtagg aggacccggc      60
cataaggcaa gagttttggc tgaagcaatg agccaagtaa caaattcagc taccataatg     120
atgcagagag gcaattttag gaaccaaaga aagattgtta agtgtttcaa ttgtggcaaa     180
gaagggcaca cagccagaaa ttgcagggcc cctaggaaaa agggctgttg gaaatgtgga     240
aaggaaggac accaaatgaa agattgtact gagagacagg ctaattttt agggaagatc     300 tggccttcct acaagggaag gccagggaat ttt ctt cag agc aga cca gag cca     354
                                    Leu Gln Ser Arg Pro Glu Pro
                                     1               5 aca gcc cca cca gaa gag agc ttc agg tct ggg gta gag aca aca act       402
Thr Ala Pro Pro Glu Glu Ser Phe Arg Ser Gly Val Glu Thr Thr Thr
             10                  15                  20 ccc cct cag aag cag gag ccg ata gac aag gaa ctg tat cct tta act       450
Pro Pro Gln Lys Gln Glu Pro Ile Asp Lys Glu Leu Tyr Pro Leu Thr
     25                  30                  35 tcc ctc agg tca ctc ttt ggc aac gac ccc tcg tca caa taaagatagg        499
Ser Leu Arg Ser Leu Phe Gly Asn Asp Pro Ser Ser Gln
 40                  45                  50 ggggcaacta aaggaagctc tattagatac aggagcagat gatacagtat tagaagaaat     559
gagtttgcca ggaagatgga aaccaaaaat gatagggga attggaggtt ttatcaaagt     619
aagacagtat gatcagatac tcatagaaat ctgtggacat aaagctatag gtacagtatt     679
agtaggacct acacctgtca acataattgg aagaaatctg ttgactcaga ttggttgcac     739
tttaaatttt cccattagcc ctattgagac tgtaccagta aaattaaagc caggaatgga     799
```

```
tggcccaaaa gttaaacaat ggccattgac agaagaaaaa ataaaagcat tagtagaaat    859
ttgtacagag atggaaaagg aagcgaaaat ttcaaaaatt gggcctgaaa atccatacaa    919
tactccagta tttgccataa agaaaaaaga cagtactaaa tggagaaaat tagtagattt    979
cagagaactt aataagagaa ctcaagactt ctgggaagtt caattaggaa taccacatcc   1039
cgcaggctta aaaagaaaaa atcagtaaca gtactggatg tgggtgatg catattttc   1099 agttccctta gatgaagact tcaggaagta tactgcattt accataccta gtataaacaa   1159
tgagacacca gggattagat atcagtacaa tgtgcttcca gggatgga aaggatcacc    1219 agcaatattc caaagtagca tgacaaaaat cttagagcct tttagaaaac aaaatccaga   1279
catagttatc tatcaataca tggatgattt gtatgtagga tctgacttag aaatagggca   1339
gcatagaaca aaaatagagg agctgagaca acatctgttg aggtggggac ttaccacacc   1399
agacaaaaaa catcagaaag aacctccatt cctttggatg ggttatgaac tccatcctga   1459
taaatggaca gtacagccta gtgctgcc agaaaaagac agctggactg tcaatgacat   1519
acagaagtta gtgggaaat tgaattgggc aagtcagatt tacccaggga ttaaagtaag   1579
gcaattatgt aaactcctta gaggaaccaa agcactaaca gaagtaatac cactaacaga   1639
agaagcagag ctagaactgg cagaaaacag agagattcta aaagaaccag tacatggagt   1699
gtattatgac ccatcaaaag acttaatagc agaaatacag aagcaggggc aaggccaatg   1759
gacatatcaa atttatcaag agccatttaa aaatctgaaa acaggaaaat atgcaagaat   1819 gagggggtgcc cacactaatg atgtaaaaca attaacagag gcagtgcaaa aaataaccac   1879
agaaagcata gtaatatggg gaaagactcc taaatttaaa ctgcccatac aaaaggaaac   1939
atgggaaaca tggtggacag agtattggca agccacctgg attcctgagt gggagtttgt   1999
taatacccct cccttagtga aattatggta ccagttagag aaagaaccca tagtaggagc   2059
agaaaccttc tatgtagatg gggcagctaa cagggagact aaattaggaa aagcaggata   2119
tgttactaat agaggaagac aaaaagttgt caccctaact gacacaacaa atcagaagac   2179
tgagttacaa gcaatttatc tagctttgca ggattcggga ttagaagtaa acatagtaac   2239
agactcacaa tatgcattag gaatcattca agcacaacca gatcaaagtg aatcagagtt   2299
agtcaatcaa ataatagagc agttaataaa aaaggaaaag gtctatctgg catgggtacc   2359
agcacacaaa ggaattggag gaaatgaaca agtagataaa ttagtcagtg ctggaatcag   2419
gaaagtacta ttttagatg aatagataa ggcccaagat gaacatgaga aatatcacag   2479
taattggaga gcaatggcta gtgattttaa cctgccacct gtagtagcaa aagaaatagt   2539
agccagctgt gataaatgtc agctaaaagg agaagccatg catggacaag tagactgtag   2599
tc                                                                 2601
```

```
<210> SEQ ID NO 10
<211> LENGTH: 52
<212> TYPE: PRT
<213> ORGANISM: HIV-HXB2

<400> SEQUENCE: 10

Leu Gln Ser Arg Pro Glu Pro Thr Ala Pro Pro Glu Glu Ser Phe Arg
  1               5                  10                  15

Ser Gly Val Glu Thr Thr Thr Pro Gln Lys Gln Glu Pro Ile Asp
             20                  25                  30

Lys Glu Leu Tyr Pro Leu Thr Ser Leu Arg Ser Leu Phe Gly Asn Asp
         35                  40                  45
```

-continued

```
Pro Ser Ser Gln
      50

<210> SEQ ID NO 11
<211> LENGTH: 2601
<212> TYPE: DNA
<213> ORGANISM: HIV-HXB2
<220> FEATURE:
<221> NAME/KEY: CDS
<222> LOCATION: (453)..(749)
<223> OTHER INFORMATION: Protease

<400> SEQUENCE: 11
ggaccagcgg ctacactaga agaaatgatg acagcatgtc agggagtagg aggacccggc      60
cataaggcaa gagttttggc tgaagcaatg agccaagtaa caaattcagc taccataatg     120
atgcagagag gcaattttag gaaccaaaga aagattgtta agtgtttcaa ttgtggcaaa     180
gaagggcaca cagccagaaa ttgcagggcc cctaggaaaa agggctgttg gaaatgtgga     240
aaggaaggac accaaatgaa agattgtact gagagacagg ctaattttttt agggaagatc     300 tggccttcct acaagggaag gccagggaat tttcttcaga gcagaccaga gccaacagcc     360
ccaccagaag agagcttcag gtctggggta gagacaacaa ctccccctca gaagcaggag     420
ccgatagaca aggaactgta tcctttaact tc cct cag gtc act ctt tgg caa       473
                                  Pro Gln Val Thr Leu Trp Gln
                                   1               5 cga ccc ctc gtc aca ata aag ata ggg ggg caa cta aag gaa gct cta       521
Arg Pro Leu Val Thr Ile Lys Ile Gly Gly Gln Leu Lys Glu Ala Leu
         10                  15                  20 tta gat aca gga gca gat gat aca gta tta gaa gaa atg agt ttg cca       569
Leu Asp Thr Gly Ala Asp Asp Thr Val Leu Glu Glu Met Ser Leu Pro
 25                  30                  35 gga aga tgg aaa cca aaa atg ata ggg gga att gga ggt ttt atc aaa       617
Gly Arg Trp Lys Pro Lys Met Ile Gly Gly Ile Gly Gly Phe Ile Lys
 40                  45                  50                  55 gta aga cag tat gat cag ata ctc ata gaa atc tgt gga cat aaa gct       665
Val Arg Gln Tyr Asp Gln Ile Leu Ile Glu Ile Cys Gly His Lys Ala
                 60                  65                  70 ata ggt aca gta tta gta gga cct aca cct gtc aac ata att gga aga       713
Ile Gly Thr Val Leu Val Gly Pro Thr Pro Val Asn Ile Ile Gly Arg
             75                  80                  85 aat ctg ttg act cag att ggt tgc act tta aat ttt cccattagcc            759
Asn Leu Leu Thr Gln Ile Gly Cys Thr Leu Asn Phe
             90                  95 ctattgagac tgtaccagta aaattaaagc caggaatgga tggcccaaaa gttaaacaat     819
ggccattgac agaagaaaaa ataaaagcat tagtagaaat ttgtacagag atggaaaagg     879
aagcgaaaat ttcaaaaatt gggcctgaaa atccatacaa tactccagta tttgccataa     939
agaaaaaaga cagtactaaa tggagaaaat tagtagattt cagagaactt aataagagaa     999
ctcaagactt ctgggaagtt caattaggaa taccacatcc cgcaggctta aaaaagaaaa    1059
aatcagtaac agtactggat gtgggtgatg catatttttc agttccctta gatgaagact    1119
tcaggaagta tactgcattt accataccta gtataaacaa tgagacacca gggattagat    1179
atcagtacaa tgtgcttcca cagggatgga aaggatcacc agcaatattc caaagtagca    1239
tgacaaaaat cttagagcct tttagaaaac aaaatccaga catagttatc tatcaataca    1299
tggatgattt gtatgtagga tctgacttag aaatagggca gcatagaaca aaaatagagg    1359
agctgagaca catctgttga aggtggggac ttaccacacc agacaaaaaa catcagaaag    1419
```

```
aacctccatt cctttggatg ggttatgaac tccatcctga taaatggaca gtacagccta    1479
tagtgctgcc agaaaaagac agctggactg tcaatgacat acagaagtta gtggggaaat    1539
tgaattgggc aagtcagatt tacccaggga ttaaagtaag gcaattatgt aaactcctta    1599
gaggaaccaa agcactaaca gaagtaatac cactaacaga agaagcagag ctagaactgg    1659
cagaaaacag agagattcta aaagaaccag tacatggagt gtattatgac ccatcaaaag    1719
acttaatagc agaaatacag aagcaggggc aaggccaatg gacatatcaa atttatcaag    1779
agccatttaa aaatctgaaa acaggaaaat atgcaagaat gaggggtgcc cacactaatg    1839
atgtaaaaca attaacagag gcagtgcaaa aaataaccac agaaagcata gtaatatggg    1899
gaaagactcc taaatttaaa ctgcccatac aaaaggaaac atgggaaaca tggtggacag    1959
agtattggca agccacctgg attcctgagt gggagtttgt taatacccct cccttagtga    2019
aattatggta ccagttagag aaagaaccca tagtaggagc agaaaccttc tatgtagatg    2079
gggcagctaa cagggagact aaattaggaa aagcaggata tgttactaat agaggaagac    2139
aaaaagttgt cacctaact gacacaacaa atcagaagac tgagttacaa gcaatttatc    2199
tagctttgca ggattcggga ttagaagtaa acatagtaac agactcacaa tatgcattag    2259
gaatcattca agcacaacca gatcaaagtg aatcagagtt agtcaatcaa ataatagagc    2319
agttaataaa aaggaaaag gtctatctgg catgggtacc agcacacaaa ggaattggag    2379
gaaatgaaca agtagataaa ttagtcagtg ctggaatcag aaagtacta ttttagatg     2439 gaatagataa ggcccaagat gaacatgaga atatcacag taattggaga gcaatggcta    2499
gtgattttaa cctgccacct gtagtagcaa agaaaatagt agccagctgt gataaatgtc    2559
agctaaaagg agaagccatg catggacaag tagactgtag tc                      2601

<210> SEQ ID NO 12
<211> LENGTH: 99
<212> TYPE: PRT
<213> ORGANISM: HIV-HXB2

<400> SEQUENCE: 12

Pro Gln Val Thr Leu Trp Gln Arg Pro Leu Val Thr Ile Lys Ile Gly
 1               5                  10                  15

Gly Gln Leu Lys Glu Ala Leu Leu Asp Thr Gly Ala Asp Asp Thr Val
            20                  25                  30

Leu Glu Glu Met Ser Leu Pro Gly Arg Trp Lys Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe

<210> SEQ ID NO 13
<211> LENGTH: 2601
<212> TYPE: DNA
<213> ORGANISM: HIV-HXB2
<220> FEATURE:
<221> NAME/KEY: CDS
<222> LOCATION: (750)..(2435)
<223> OTHER INFORMATION: Reverse Transcriptase
```

<400> SEQUENCE: 13

```
ggaccagcgg ctacactaga agaaatgatg acagcatgtc agggagtagg aggacccggc    60
cataaggcaa gagttttggc tgaagcaatg agccaagtaa caaattcagc taccataatg   120
atgcagagag gcaattttag gaaccaaaga aagattgtta agtgtttcaa ttgtggcaaa   180
gaagggcaca cagccagaaa ttgcagggcc cctaggaaaa agggctgttg gaaatgtgga   240
aaggaaggac accaaatgaa agattgtact gagagacagg ctaattttt agggaagatc    300
tggccttcct acaagggaag ccagggaat tttcttcaga gcagaccaga gccaacagcc    360
ccaccagaag agagcttcag gtctggggta gagacaacaa ctcccctca gaagcaggag    420
ccgatagaca aggaactgta tcctttaact ccctcaggt cactctttgg caacgacccc    480
tcgtcacaat aaagataggg gggcaactaa aggaagctct attagataca ggagcagatg   540
atacagtatt agaagaaatg agtttgccag gaagatggaa accaaaaatg ataggggaa    600
ttggaggttt tatcaaagta agacagtatg atcagatact catagaaatc tgtggacata   660
aagctatagg tacagtatta gtaggaccta cacctgtcaa cataattgga agaaatctgt   720
tgactcagat tggttgcact ttaaatttt ccc att agc cct att gag act gta     773
                                    Pro Ile Ser Pro Ile Glu Thr Val
                                     1               5
cca gta aaa tta aag cca gga atg gat ggc cca aaa gtt aaa caa tgg     821
Pro Val Lys Leu Lys Pro Gly Met Asp Gly Pro Lys Val Lys Gln Trp
 10              15                  20
cca ttg aca gaa gaa aaa ata aaa gca tta gta gaa att tgt aca gag     869
Pro Leu Thr Glu Glu Lys Ile Lys Ala Leu Val Glu Ile Cys Thr Glu
 25              30                  35                  40
atg gaa aag gaa gcg aaa att tca aaa att ggg cct gaa aat cca tac     917
Met Glu Lys Glu Ala Lys Ile Ser Lys Ile Gly Pro Glu Asn Pro Tyr
             45                  50                  55
aat act cca gta ttt gcc ata aag aaa aaa gac agt act aaa tgg aga     965
Asn Thr Pro Val Phe Ala Ile Lys Lys Lys Asp Ser Thr Lys Trp Arg
         60                  65                  70
aaa tta gta gat ttc aga gaa ctt aat aag aga act caa gac ttc tgg    1013
Lys Leu Val Asp Phe Arg Glu Leu Asn Lys Arg Thr Gln Asp Phe Trp
     75                  80                  85
gaa gtt caa tta gga ata cca cat ccc gca ggc tta aaa aag aaa aaa    1061
Glu Val Gln Leu Gly Ile Pro His Pro Ala Gly Leu Lys Lys Lys Lys
 90                  95                 100
tca gta aca gta ctg gat gtg ggt gat gca tat ttt tca gtt ccc tta    1109
Ser Val Thr Val Leu Asp Val Gly Asp Ala Tyr Phe Ser Val Pro Leu
105                 110                 115                 120
gat gaa gac ttc agg aag tat act gca ttt acc ata cct agt ata aac    1157
Asp Glu Asp Phe Arg Lys Tyr Thr Ala Phe Thr Ile Pro Ser Ile Asn
                125                 130                 135
aat gag aca cca ggg att aga tat cag tac aat gtg ctt cca cag gga    1205
Asn Glu Thr Pro Gly Ile Arg Tyr Gln Tyr Asn Val Leu Pro Gln Gly
            140                 145                 150
tgg aaa gga tca cca gca ata ttc caa agt agc atg aca aaa atc tta    1253
Trp Lys Gly Ser Pro Ala Ile Phe Gln Ser Ser Met Thr Lys Ile Leu
        155                 160                 165
gag cct ttt aga aaa caa aat cca gac ata gtt atc tat caa tac atg    1301
Glu Pro Phe Arg Lys Gln Asn Pro Asp Ile Val Ile Tyr Gln Tyr Met
    170                 175                 180
gat gat ttg tat gta gga tct gac tta gaa ata ggg cag cat aga aca    1349
Asp Asp Leu Tyr Val Gly Ser Asp Leu Glu Ile Gly Gln His Arg Thr
185                 190                 195                 200
aaa ata gag gag ctg aga caa cat ctg ttg agg tgg gga ctt acc aca    1397
```

```
                Lys Ile Glu Glu Leu Arg Gln His Leu Leu Arg Trp Gly Leu Thr Thr
                                205                 210                 215 cca gac aaa aaa cat cag aaa gaa cct cca ttc ctt tgg atg ggt tat       1445
Pro Asp Lys Lys His Gln Lys Glu Pro Pro Phe Leu Trp Met Gly Tyr
            220                 225                 230 gaa ctc cat cct gat aaa tgg aca gta cag cct ata gtg ctg cca gaa       1493
Glu Leu His Pro Asp Lys Trp Thr Val Gln Pro Ile Val Leu Pro Glu
        235                 240                 245 aaa gac agc tgg act gtc aat gac ata cag aag tta gtg ggg aaa ttg       1541
Lys Asp Ser Trp Thr Val Asn Asp Ile Gln Lys Leu Val Gly Lys Leu
    250                 255                 260 aat tgg gca agt cag att tac cca ggg att aaa gta agg caa tta tgt       1589
Asn Trp Ala Ser Gln Ile Tyr Pro Gly Ile Lys Val Arg Gln Leu Cys
265                 270                 275                 280 aaa ctc ctt aga gga acc aaa gca cta aca gaa gta ata cca cta aca       1637
Lys Leu Leu Arg Gly Thr Lys Ala Leu Thr Glu Val Ile Pro Leu Thr
                285                 290                 295 gaa gaa gca gag cta gaa ctg gca gaa aac aga gag att cta aaa gaa       1685
Glu Glu Ala Glu Leu Glu Leu Ala Glu Asn Arg Glu Ile Leu Lys Glu
            300                 305                 310 cca gta cat gga gtg tat tat gac cca tca aaa gac tta ata gca gaa       1733
Pro Val His Gly Val Tyr Tyr Asp Pro Ser Lys Asp Leu Ile Ala Glu
        315                 320                 325 ata cag aag cag ggg caa ggc caa tgg aca tat caa att tat caa gag       1781
Ile Gln Lys Gln Gly Gln Gly Gln Trp Thr Tyr Gln Ile Tyr Gln Glu
    330                 335                 340 cca ttt aaa aat ctg aaa aca gga aaa tat gca aga atg agg ggt gcc       1829
Pro Phe Lys Asn Leu Lys Thr Gly Lys Tyr Ala Arg Met Arg Gly Ala
345                 350                 355                 360 cac act aat gat gta aaa caa tta aca gag gca gtg caa aaa ata acc       1877
His Thr Asn Asp Val Lys Gln Leu Thr Glu Ala Val Gln Lys Ile Thr
                365                 370                 375 aca gaa agc ata gta ata tgg gga aag act cct aaa ttt aaa ctg ccc       1925
Thr Glu Ser Ile Val Ile Trp Gly Lys Thr Pro Lys Phe Lys Leu Pro
            380                 385                 390 ata caa aag gaa aca tgg gaa aca tgg tgg aca gag tat tgg caa gcc       1973
Ile Gln Lys Glu Thr Trp Glu Thr Trp Trp Thr Glu Tyr Trp Gln Ala
        395                 400                 405 acc tgg att cct gag tgg gag ttt gtt aat acc cct ccc tta gtg aaa       2021
Thr Trp Ile Pro Glu Trp Glu Phe Val Asn Thr Pro Pro Leu Val Lys
    410                 415                 420 tta tgg tac cag tta gag aaa gaa ccc ata gta gga gca gaa acc ttc       2069
Leu Trp Tyr Gln Leu Glu Lys Glu Pro Ile Val Gly Ala Glu Thr Phe
425                 430                 435                 440 tat gta gat ggg gca gct aac agg gag act aaa tta gga aaa gca gga       2117
Tyr Val Asp Gly Ala Ala Asn Arg Glu Thr Lys Leu Gly Lys Ala Gly
                445                 450                 455 tat gtt act aat aga gga aga caa aaa gtt gtc acc cta act gac aca       2165
Tyr Val Thr Asn Arg Gly Arg Gln Lys Val Val Thr Leu Thr Asp Thr
            460                 465                 470 aca aat cag aag act gag tta caa gca att tat cta gct ttg cag gat       2213
Thr Asn Gln Lys Thr Glu Leu Gln Ala Ile Tyr Leu Ala Leu Gln Asp
        475                 480                 485 tcg gga tta gaa gta aac ata gta aca gac tca caa tat gca tta gga       2261
Ser Gly Leu Glu Val Asn Ile Val Thr Asp Ser Gln Tyr Ala Leu Gly
    490                 495                 500 atc att caa gca caa cca gat caa agt gaa tca gag tta gtc aat caa       2309
Ile Ile Gln Ala Gln Pro Asp Gln Ser Glu Ser Glu Leu Val Asn Gln
505                 510                 515                 520
```

-continued

```
ata ata gag cag tta ata aaa aag gaa aag gtc tat ctg gca tgg gta    2357
Ile Ile Glu Gln Leu Ile Lys Lys Glu Lys Val Tyr Leu Ala Trp Val
                525                 530                 535 cca gca cac aaa gga att gga gga aat gaa caa gta gat aaa tta gtc    2405
Pro Ala His Lys Gly Ile Gly Gly Asn Glu Gln Val Asp Lys Leu Val
            540                 545                 550 agt gct gga atc agg aaa gta cta ttt tta gatggaatag ataaggccca      2455
Ser Ala Gly Ile Arg Lys Val Leu Phe Leu
        555                 560 agatgaacat gagaaatatc acagtaattg gagagcaatg ctagtgatt ttaacctgcc   2515 acctgtagta gcaaaagaaa tagtagccag ctgtgataaa tgtcagctaa aaggagaagc  2575
catgcatgga caagtagact gtagtc                                      2601
```

<210> SEQ ID NO 14
<211> LENGTH: 562
<212> TYPE: PRT
<213> ORGANISM: HIV-HXB2

<400> SEQUENCE: 14

```
Pro Ile Ser Pro Ile Glu Thr Val Pro Val Lys Leu Lys Pro Gly Met
 1               5                  10                  15

Asp Gly Pro Lys Val Lys Gln Trp Pro Leu Thr Glu Glu Lys Ile Lys
            20                  25                  30

Ala Leu Val Glu Ile Cys Thr Glu Met Glu Lys Glu Ala Lys Ile Ser
        35                  40                  45

Lys Ile Gly Pro Glu Asn Pro Tyr Asn Thr Pro Val Phe Ala Ile Lys
    50                  55                  60

Lys Lys Asp Ser Thr Lys Trp Arg Lys Leu Val Asp Phe Arg Glu Leu
65                  70                  75                  80

Asn Lys Arg Thr Gln Asp Phe Trp Glu Val Gln Leu Gly Ile Pro His
                85                  90                  95

Pro Ala Gly Leu Lys Lys Lys Ser Val Thr Val Leu Asp Val Gly
            100                 105                 110

Asp Ala Tyr Phe Ser Val Pro Leu Asp Glu Asp Phe Arg Lys Tyr Thr
        115                 120                 125

Ala Phe Thr Ile Pro Ser Ile Asn Asn Glu Thr Pro Gly Ile Arg Tyr
    130                 135                 140

Gln Tyr Asn Val Leu Pro Gln Gly Trp Lys Gly Ser Pro Ala Ile Phe
145                 150                 155                 160

Gln Ser Ser Met Thr Lys Ile Leu Glu Pro Phe Arg Lys Gln Asn Pro
                165                 170                 175

Asp Ile Val Ile Tyr Gln Tyr Met Asp Asp Leu Tyr Val Gly Ser Asp
            180                 185                 190

Leu Glu Ile Gly Gln His Arg Thr Lys Ile Glu Glu Leu Arg Gln His
        195                 200                 205

Leu Leu Arg Trp Gly Leu Thr Thr Pro Asp Lys Lys His Gln Lys Glu
    210                 215                 220

Pro Pro Phe Leu Trp Met Gly Tyr Glu Leu His Pro Asp Lys Trp Thr
225                 230                 235                 240

Val Gln Pro Ile Val Leu Pro Glu Lys Asp Ser Trp Thr Val Asn Asp
                245                 250                 255

Ile Gln Lys Leu Val Gly Lys Leu Asn Trp Ala Ser Gln Ile Tyr Pro
            260                 265                 270

Gly Ile Lys Val Arg Gln Leu Cys Lys Leu Leu Arg Gly Thr Lys Ala
        275                 280                 285
```

```
Leu Thr Glu Val Ile Pro Leu Thr Glu Glu Ala Glu Leu Glu Leu Ala
    290                 295                 300

Glu Asn Arg Glu Ile Leu Lys Glu Pro Val His Gly Val Tyr Asp
305             310                 315                 320

Pro Ser Lys Asp Leu Ile Ala Glu Ile Gln Lys Gln Gly Gln Gly Gln
                325                 330                 335

Trp Thr Tyr Gln Ile Tyr Gln Glu Pro Phe Lys Asn Leu Lys Thr Gly
            340                 345                 350

Lys Tyr Ala Arg Met Arg Gly Ala His Thr Asn Asp Val Lys Gln Leu
            355                 360                 365

Thr Glu Ala Val Gln Lys Ile Thr Thr Glu Ser Ile Val Ile Trp Gly
    370                 375                 380

Lys Thr Pro Lys Phe Lys Leu Pro Ile Gln Lys Glu Thr Trp Glu Thr
385                 390                 395                 400

Trp Trp Thr Glu Tyr Trp Gln Ala Thr Trp Ile Pro Glu Trp Glu Phe
                405                 410                 415

Val Asn Thr Pro Pro Leu Val Lys Leu Trp Tyr Gln Leu Glu Lys Glu
                420                 425                 430

Pro Ile Val Gly Ala Glu Thr Phe Tyr Val Asp Gly Ala Ala Asn Arg
                435                 440                 445

Glu Thr Lys Leu Gly Lys Ala Gly Tyr Val Thr Asn Arg Gly Arg Gln
    450                 455                 460

Lys Val Val Thr Leu Thr Asp Thr Thr Asn Gln Lys Thr Glu Leu Gln
465                 470                 475                 480

Ala Ile Tyr Leu Ala Leu Gln Asp Ser Gly Leu Glu Val Asn Ile Val
                485                 490                 495

Thr Asp Ser Gln Tyr Ala Leu Gly Ile Ile Gln Ala Gln Pro Asp Gln
            500                 505                 510

Ser Glu Ser Glu Leu Val Asn Gln Ile Ile Glu Gln Leu Ile Lys Lys
        515                 520                 525

Glu Lys Val Tyr Leu Ala Trp Val Pro Ala His Lys Gly Ile Gly Gly
    530                 535                 540

Asn Glu Gln Val Asp Lys Leu Val Ser Ala Gly Ile Arg Lys Val Leu
545                 550                 555                 560

Phe Leu

<210> SEQ ID NO 15
<211> LENGTH: 13
<212> TYPE: DNA
<213> ORGANISM: Partial sequence of plasmid pGEMT3...

<400> SEQUENCE: 15
gacccgggtg acc                                                          13
```